US009170351B2

(12) United States Patent
Natsumeda et al.

(10) Patent No.: US 9,170,351 B2
(45) Date of Patent: Oct. 27, 2015

(54) OPTICAL ELEMENT, LIGHT SOURCE APPARATUS, AND PROJECTION-TYPE DISPLAY APPARATUS

(75) Inventors: Masanao Natsumeda, Tokyo (JP); Masao Imai, Tokyo (JP); Naofumi Suzuki, Tokyo (JP); Mizuho Tomiyama, Tokyo (JP); Shin Tominaga, Tokyo (JP); Yuji Ohno, Tokyo (JP)

(73) Assignee: NEC Corporation, Tokyo (JP)

( * ) Notice: Subject to any disclaimer, the term of this patent is extended or adjusted under 35 U.S.C. 154(b) by 126 days.

(21) Appl. No.: 14/126,038

(22) PCT Filed: Apr. 6, 2012

(86) PCT No.: PCT/JP2012/059474
§ 371 (c)(1),
(2), (4) Date: Dec. 13, 2013

(87) PCT Pub. No.: WO2012/172858
PCT Pub. Date: Dec. 20, 2012

(65) Prior Publication Data
US 2014/0139809 A1    May 22, 2014

(30) Foreign Application Priority Data

Jun. 17, 2011   (JP) .................................. 2011-135032
Jan. 6, 2012    (JP) .................................. 2012-001322

(51) Int. Cl.
*G03B 21/20*    (2006.01)
*G02B 5/00*     (2006.01)
(Continued)

(52) U.S. Cl.
CPC .............. *G02B 5/008* (2013.01); *G01N 21/553* (2013.01); *G01N 21/648* (2013.01); *G02B 6/005* (2013.01);
(Continued)

(58) Field of Classification Search
CPC .... G03B 21/00; G03B 21/20; G03B 21/2033; G03B 21/204; G02B 5/008; G02B 6/005; G01N 21/552–21/554; G01N 21/648; H01L 51/5262; F21V 9/00
See application file for complete search history.

(56) References Cited

U.S. PATENT DOCUMENTS 9,028,071 B2 *  5/2015  Natsumeda et al. ............ 353/20
9,039,201 B2 *  5/2015  Natsumeda et al. ............ 353/88
(Continued)

FOREIGN PATENT DOCUMENTS

JP    2007-214260    8/2007
JP    2008-145510    6/2008
(Continued)

OTHER PUBLICATIONS

International Search Report corresponding to PCT/JP2012/059474, dated Jun. 29, 2012, 3 pages.
(Continued)

*Primary Examiner* — Jori S Reilly-Diakun
(74) *Attorney, Agent, or Firm* — Wilmer Cutler Pickering Hale and Dorr LLP

(57) ABSTRACT

An optical element that can reduce the etendue of emitted light emitted from the optical element without having depend on the etendue of light-emitting elements is provided with a plasmon-excitation layer that is interposed between two layers having dielectric properties wherein, taking the plasmon-excitation layer as a border, the effective dielectric constant of the emission-side portion that is the emission layer side is higher than the effective dielectric constant of the incident-side portion that is the side of a carrier-generating layer, and the dielectric constant between the plasmon-excitation layer and the carrier-generating layer is higher than the dielectric constant between the carrier-generating layer and the light-incident surface.

14 Claims, 18 Drawing Sheets

(51) Int. Cl.
*G01N 21/64* (2006.01)
*G01N 21/552* (2014.01)
*F21V 8/00* (2006.01)
*G02F 1/1335* (2006.01)

(52) U.S. Cl.
CPC .......... G03B 21/204 (2013.01); G03B 21/2033 (2013.01); G02F 1/133602 (2013.01); G02F 1/133606 (2013.01); G03B 21/2073 (2013.01)

(56) References Cited

U.S. PATENT DOCUMENTS

| | | | |
|---|---|---|---|
| 9,041,041 B2 * | 5/2015 | Natsumeda et al. | 257/98 |
| 2003/0184989 A1 * | 10/2003 | Matsumoto et al. | 362/19 |
| 2006/0278888 A1 * | 12/2006 | Kim et al. | 257/103 |
| 2007/0181889 A1 | 8/2007 | Orita | |
| 2011/0260602 A1 * | 10/2011 | Lee et al. | 313/491 |
| 2012/0314188 A1 * | 12/2012 | Tominaga et al. | 353/20 |
| 2012/0314189 A1 * | 12/2012 | Natsumeda et al. | 353/20 |
| 2013/0033678 A1 * | 2/2013 | Natsumeda et al. | 353/20 |
| 2013/0308102 A1 * | 11/2013 | Natsumeda et al. | 353/20 |
| 2014/0022818 A1 * | 1/2014 | Natsumeda et al. | 362/607 |

FOREIGN PATENT DOCUMENTS

| | | |
|---|---|---|
| JP | 2009-087695 | 4/2009 |
| WO | WO-2011/040528 | 4/2011 |

OTHER PUBLICATIONS

Hoepfner, C., "PhatLight™ Phototonic Lattice LEDs for RPTV Light Engines", SID Symposium Digest 37, 2006, 4 pages.

* cited by examiner (a)　　　　　　　　　(b)

OPTICAL ELEMENT, LIGHT SOURCE APPARATUS, AND PROJECTION-TYPE DISPLAY APPARATUS

CROSS-REFERENCE TO RELATED APPLICATIONS

This application is a national stage application of International Application No. PCT/JP2012/059474 entitled "Optical Element, Light Source Apparatus, and Projection-type Display Apparatus," filed on Apr. 6, 2012, which claims the benefit of the priority of Japanese Patent Application No. 2011-135032, filed on Jun. 17, 2011, and Japanese Patent Application No. 2012-001322, filed on Jan. 6, 2012, the disclosures of each of which are hereby incorporated by reference in their entirety.

TECHNICAL FIELD

The present invention relates to an optical element, a light source apparatus, and a projection-type display apparatus that use plasmon coupling to emit light.

BACKGROUND ART

LED projectors have been proposed in which light-emitting diodes (LEDs) are used as the light-emitting devices included in the light source apparatuses. This type of LED projector is configured equipped with a light source apparatus having LEDs, an illumination optical system into which light emitted from the light source apparatus is irradiated, a light valve having a liquid crystal display panel into which light from the illumination optical system is irradiated, and a projection optical system for projecting light from the light valve onto a projection surface.

In order to increase the luminance of an image that is projected by an LED projector, all possible measures need to be taken to eliminate light loss in the optical path from the light source apparatus to the light valve.

In addition, as disclosed in Non-Patent Document 1 discloses limitations caused by etendue, which is determined by the product of the surface area of the light source apparatus and the angle of radiation. In other words, light from the light source apparatus is not utilized as projection light if the value of the product of the angle of radiation and the surface area of light emission of the light source apparatus is not made equal to or lower than the value of the product of the surface area of the incident surface of the light valve and the acceptance angle (solid angle) that is determined by the f-number of the projection lens.

As a result, in a light source apparatus that has LEDs and an optical element into which light from the LEDs is irradiated, realizing a reduction of the above-described light loss by decreasing the etendue of light emitted from the optical element remains an unresolved problem.

In a light source apparatus that is equipped in an LED projector, it is absolutely imperative that a plurality of LEDs be employed to compensate for the insufficient amount of light generated by a single LED of a single LED and thus realize projected luminous flux on the order of several thousand lumens.

As one example of a light source apparatus that uses a plurality of LEDs in this way, Patent Document 1 discloses a light source unit, as shown in FIG. 1, that is equipped with: a plurality of monochromatic light source apparatuses 83a-83f having LEDs 84a-84f, optical axis alignment parts 82a-82d that cause the optical axes of light emitted from these monochromatic light source apparatuses 83a-83f to coincide, light source sets 81a and 81b into which light from these optical axis alignment parts 82a-82d is irradiated, and light guide apparatus 80 into which light from these light source sets 81a and 81b is irradiated. In this light source unit, light from the plurality of monochromatic light source apparatuses 83a-83f is synthesized, and light for which the angle of radiation has been constricted by light source sets 81a and 81b is irradiated into light guide apparatus 80. In this configuration, a reduction of light loss is achieved by light source sets 81a and 81b that constrict the angle of radiation of light that is irradiated into light guide apparatus 80.

Alternatively, as another example of a light source apparatus that uses a plurality of LEDs, Patent Document 2 discloses a light source apparatus as shown in FIG. 2 that is equipped with light source substrate 86 on which a plurality of LEDs 85 are arranged on a plane. This light source apparatus is provided with an optical element composed of two prism sheets 88 and 89 that each have prism rows formed on one surface and that are each arranged such that the prism rows of one sheet are orthogonal to the prism rows of the other, and frame 87 that supports these prism sheets 88 and 89. In this light source apparatus, light from the plurality of LEDs 85 is synthesized by the two prism sheets 88 and 89.

LITERATURE OF THE PRIOR ART

Patent Documents

Patent Document 1: Japanese Unexamined Patent Application Publication No. 2008-145510
Patent Document 2: Japanese Unexamined Patent Application Publication No. 2009-087695

Non-Patent Documents

Non-Patent Document 1: Christian Hoepfner, (2006) PhlatLight™ Photonic Lattice LEDs for RPTV Light Engines. *SID Symposium. Digest* 37, 1808.

SUMMARY OF THE INVENTION

Problem to be Solved by the Invention

However, in the configuration disclosed in the above-described Patent Document 1, the light-emitting area on the dichroic reflection surfaces of optical axis alignment parts 82a-82d is greater than the light-emitting area of LEDs 84a-84f, and as a result, a comparison of the etendue of light that is irradiated into light guide apparatus 80 with the etendue of light from LEDs 84a-84f shows no change in etendue.

Accordingly, in the configuration disclosed in Patent Document 1, the etendue of light emitted from light guide apparatus 80 depends on the etendue of LEDs 84a-84f, and a reduction of the etendue of light emitted from light guide apparatus 80 was not possible.

In the configuration disclosed in Patent Document 2, the light-emitting area of the entire light source is enlarged due to the arrangement of a plurality of LEDs 85 in rows on a planar surface, whereby the problem arises that the etendue of the light source itself is increased.

In other words, in the configurations disclosed in the above-described Patent Documents 1 and 2, the etendue of light emitted from the light source unit and light source apparatus is dependent on the etendue of light from LEDs, and the etendue of light emitted from the optical elements could not be reduced.

It is therefore an object of the present invention to provide an optical element that solves the problems of the above-described related art and that enables a reduction of the etendue of light emitted from the optical element without having to depend on the etendue of the light-emitting elements, and to provide a light source apparatus and a projection-type display apparatus that are equipped with this optical element.

Means for Solving the Problem

The optical element according to the present invention for achieving the above-described object includes:
an incident surface into which light is irradiated;
a carrier-generating layer that is laminated on the incident surface and in which carriers are generated by light;
a plasmon-excitation layer that is laminated on the carrier-generating layer and that has higher plasma frequency than the frequency of light that is generated when the carrier-generating layer is excited by light that is irradiated from the incident surface; and
an emission layer that is laminated on the plasmon-excitation layer and that converts light irradiated from the plasmon-excitation layer to a predetermined angle of emission and emits the light;
wherein:
the plasmon-excitation layer is interposed between two layers having a dielectric property;
taking the plasmon-excitation layer as a border, the effective dielectric constant of the emission-side portion that is the emission-layer side is higher than the effective dielectric constant of the incident-side portion that is the carrier-generating layer side; and
the dielectric constant between the plasmon-excitation layer and the carrier-generating layer is higher than the dielectric constant between the carrier-generating layer and the incident surface.

The light source apparatus according to the present invention is provided with the optical element of the present invention and light-emitting elements that are arranged on the outer periphery of the light guide body.

The projection-type display apparatus according to the present invention is provided with the light source apparatus of the present invention and a projection optical system that projects a projected image by means of the light emitted from the light source apparatus.

Effect of the Invention

According to the present invention, the etendue of the light emitted from an optical element can be reduced without having to depend on the etendue of light-emitting elements.

BEST MODE FOR CARRYING OUT THE INVENTION

Specific exemplary embodiments of the present invention are next described with reference to the accompanying drawings.

First Exemplary Embodiment

Figure 1:
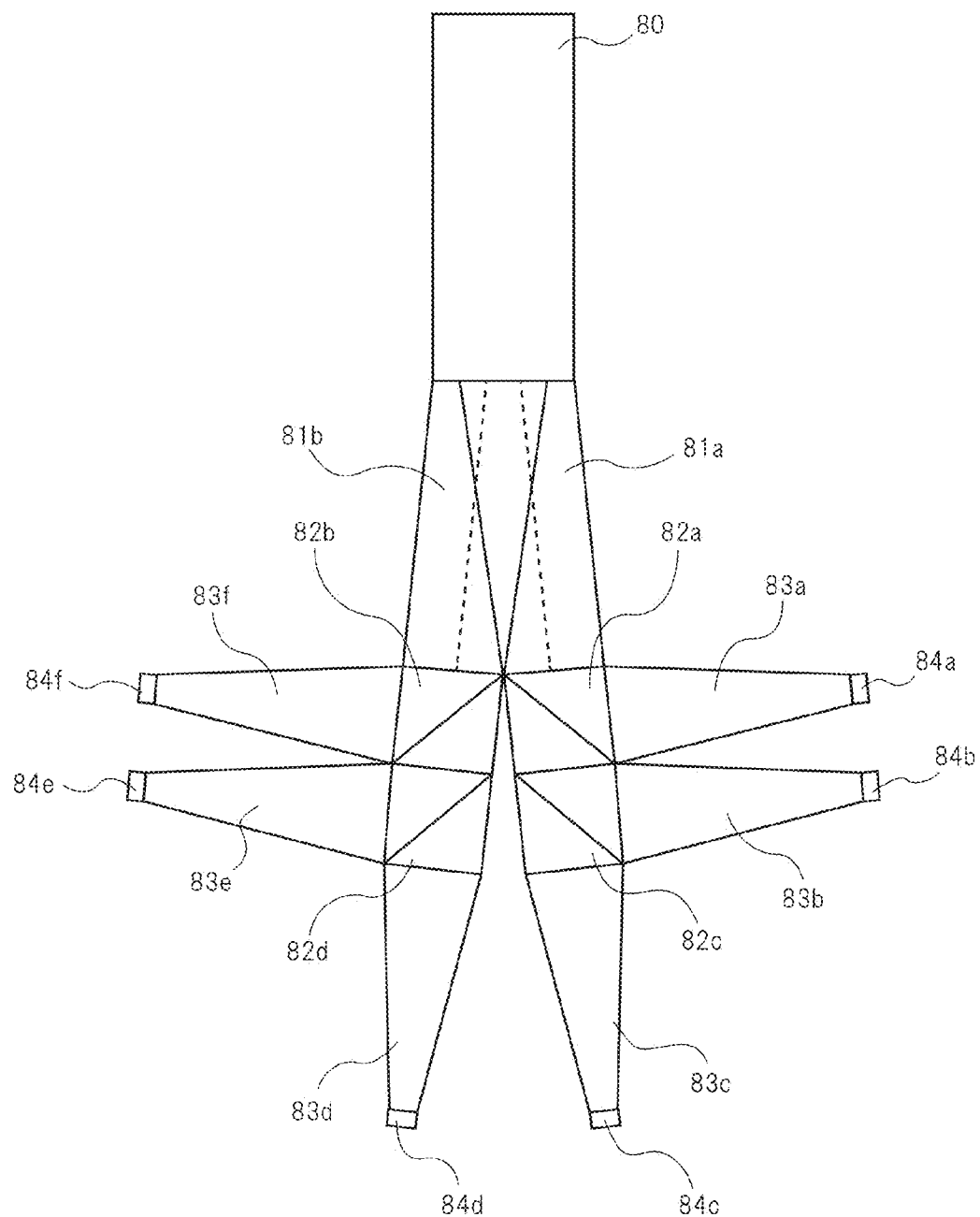
FIG. 1 is a schematic view for describing the configuration of Patent Document 1.
Figure 2:
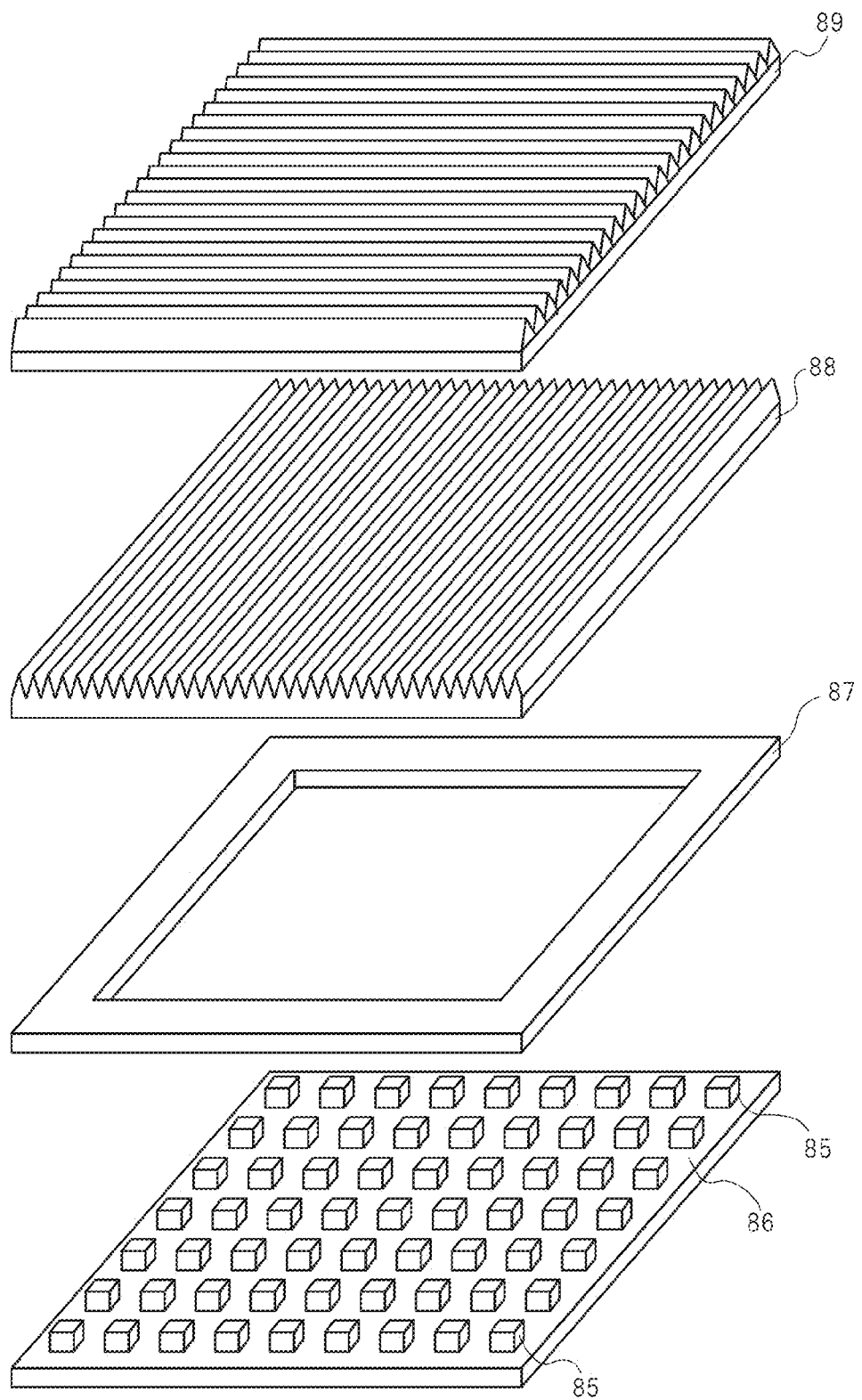
FIG. 2 is an exploded perspective view for describing the configuration of Patent Document 2.
Figure 3:
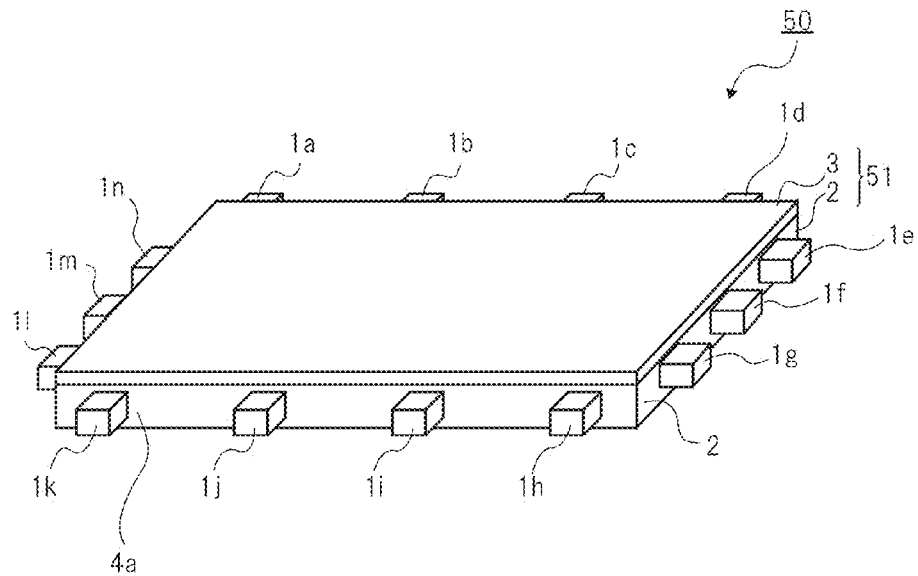
FIG. 3 is a schematic perspective view of the light source apparatus of the first exemplary embodiment of the present invention.
Figure 4A:
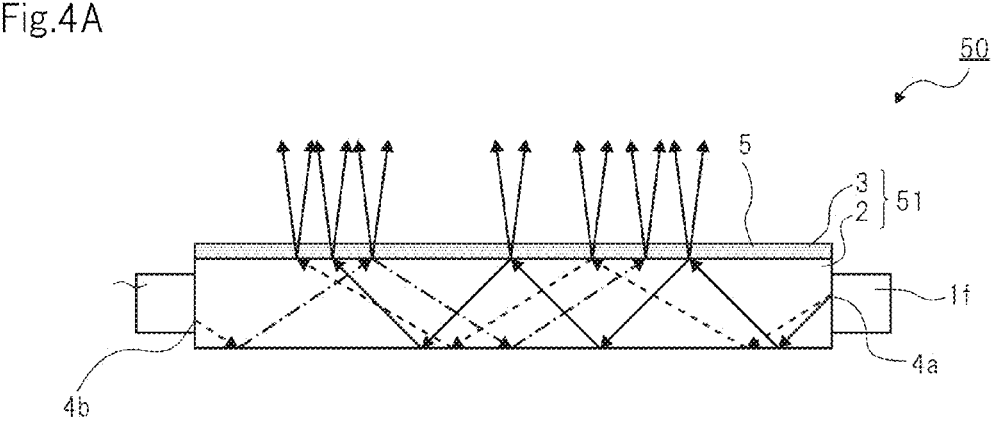
FIG. 4A is a sectional view for describing the behavior of light in the light source apparatus of the first exemplary embodiment of the present invention.

FIG. 3 is a schematic perspective view of the configuration of the light source apparatus of the present exemplary embodiment. FIG. 4A shows a sectional view for describing the behavior of light in the light source apparatus according to the present invention. Because the actual layers in the light source apparatus are each extremely thin and the differences in thickness between each of the layers are relatively great, a depiction that is drawn accurately to scale and proportion for each layer would be difficult. As a result, the layers in the drawings are each shown schematically and are not depicted according to their actual proportions.

As shown in FIGS. 3 and 4A, light source apparatus 50 of the present exemplary embodiment is equipped with a plurality of light-emitting elements (1a-1n) and optical element 51 into which light emitted from these light-emitting elements 1 is irradiated. Optical element 51 includes light guide body 2 into which light emitted from light-emitting elements 1 is irradiated and directivity control layer 3 that emits the emitted light realized by the light from this light guide body 2.

Figure 5A:
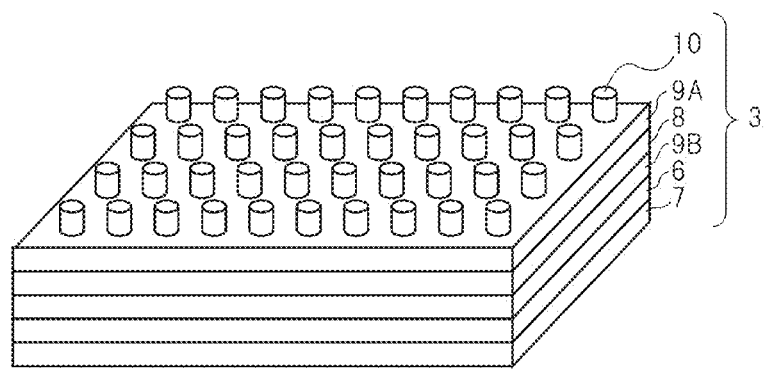
FIG. 5A is a schematic perspective view showing the directivity control layer provided in the light source apparatus of the first exemplary embodiment.
Figure 5B:
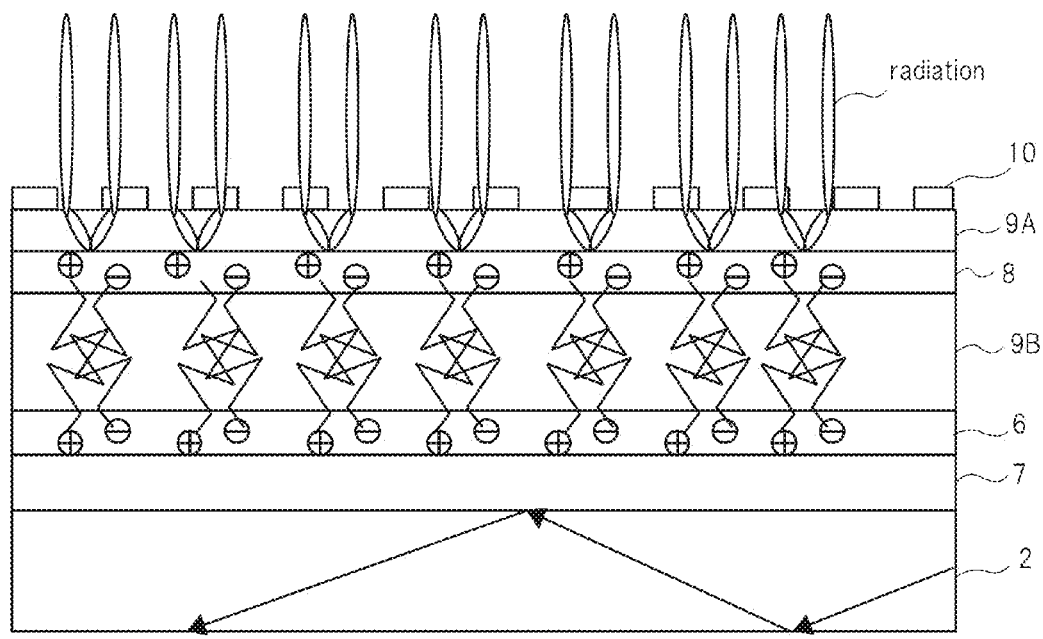
FIG. 5B is a schematic sectional view showing the directivity control layer provided in the light source apparatus of the first exemplary embodiment.

Directivity control layer 3 is a layer for raising the directivity of the light emitted from light source apparatus 50, and as in the first exemplary embodiment shown in, for example, FIGS. 5A and 5B, is provided on light guide body 2 and is equipped with: carrier-generating layer 6 that is provided on light guide body 2 and that generates carriers by means of a portion of the light that is incident from light guide body 2; plasmon-excitation layer 8 that is laminated on this carrier-generating layer 6 and that has a plasma frequency that is higher than the frequency of light that is generated when carrier-generating layer 6 is excited by the light of light-emitting elements 1; and wave vector conversion layer 10 that is laminated on this plasmon-excitation layer 8 as an emission layer that converts the wave vector of irradiated light to emit the resultant light.

In addition, plasmon-excitation layer 8 is interposed between two layers having dielectric properties. As shown in FIG. 5A and FIG. 5B, as the two layers having dielectric properties, directivity control layer 3 is provided with high dielectric constant layer 9A that is interposed between plasmon-excitation layer 8 and wave vector conversion layer 10 and high dielectric constant layer 9B that is interposed between carrier-generating layer 6 and plasmon-excitation layer 8. Directivity control layer 3 is further provided with low dielectric constant layer 7 that has a lower dielectric constant than high dielectric constant layers 9A and 9B and that is provided between light guide body 2 and carrier-generating layer 6. In the present exemplary embodiment, the interface between low dielectric constant layer 7 and light guide body 2 is the incident surface.

Optical element 1 in the present exemplary embodiment is configured such that the effective dielectric constant of the incident-side portion that includes the entire construction that is laminated on light guide body 2-side of plasmon-excitation layer 8 (hereinbelow referred to as simply "the incident-side portion") is lower than the effective dielectric constant of the emission-side portion that includes the entire construction that is laminated on wave vector conversion layer 10-side of plasmon-excitation layer 8 and the medium that makes contact with wave vector conversion layer 10 (hereinbelow referred to as the "emission-side portion"). Light guide body 2 is included in the entire construction that is laminated on the light guide body 2-side of plasmon-excitation layer 8. Wave vector conversion layer 10 is included in the entire construction that is laminated on the wave vector conversion layer 10-side of plasmon-excitation layer 8.

Essentially, in the first exemplary embodiment, the effective dielectric constant of the incident-side portion that includes light guide body 2 and carrier-generating layer 6 with respect to plasmon-excitation layer 8 is lower than the effective dielectric constant of the emission-side portion that includes wave vector conversion layer 10 and the medium with respect to plasmon-excitation layer 8.

To state in greater detail, the real part of the effective dielectric constant of the incident-side portion (the side of light-emitting elements 1) of plasmon-excitation layer 8 is set lower than the real part of the effective dielectric constant of the emission-side portion (the side of wave vector conversion layer 10) of plasmon-excitation layer 8.

Here, if the x-axis and y-axis are directions that are parallel to the interface with plasmon-excitation layer 8 and the z-axis is the direction that is perpendicular to the interface with plasmon-excitation layer 8, $\omega$ is the angular frequency of light that is emitted from carrier-generating layer 6, $\in(\omega, x, y, z)$ is the dielectric constant distribution of a dielectric in the incident-side portion and emission-side portion with respect to plasmon-excitation layer 8, $k_{spp,z}$ is the z-component of the wave number of surface plasmons, and j is an imaginary unit, then the effective dielectric constant $\in_{\text{eff}}$ is determined based on the dielectric constant distribution of the incident-side portion or emission-side portion and the distribution of surface plasmons with respect to the direction that is perpendicular to the interface of plasmon-excitation layer 8, and is expressed by:

$$\varepsilon_{eff} = \frac{\int\int_D\int \text{Re}[\varepsilon(\omega, x, y, z)]\exp(2jk_{spp,z}z)}{\int\int_D\int \exp(2jk_{spp,z}z)} \quad \text{equation (1)}$$

Here, integration range D is the range of three-dimensional coordinates of the incident-side portion or emission-side portion with respect to plasmon-excitation layer 8. In other words, the range in the x-axis direction and y-axis direction of this integration range D is the range, not including the medium, of the construction included by the incident-side portion as far as the outer peripheral surface or the construction included by the emission-side portion as far as the outer peripheral surface, and is a range that extends to the outer edge within a plane that is parallel to the interface with plasmon-excitation layer 8. The range in the z-axis direction in integration range D is the range of the incident-side portion or emission-side portion (including the medium).

The effective dielectric constant $\varepsilon_{eff}$ may be calculated using the following equation. The use of Equation (1.1) is particularly preferable.

$$\varepsilon_{eff} = \left(\frac{\int\int_D\int \text{Re}[\sqrt{\varepsilon(\omega, x, y, z)}]\exp(2jk_{spp,z}z)}{\int\int_D\int \exp(2jk_{spp,z}z)}\right)^2 \quad \text{equation (1.1)}$$

In addition, if $\varepsilon_{metal}$ is the dielectric constant of plasmon-excitation layer 8 and $k_0$ is the wave number of light in a vacuum, the z component $k_{spp,z}$ of the wave number of surface plasmons and the x- and y-components $k_{spp}$ of the wave number of surface plasmons are expressed by:

$$k_{spp,z} = \sqrt{\varepsilon_{eff}k_0^2 - k_{spp}^2} \quad \text{equation (2)}$$

$$k_{spp} = k_0\text{Re}\left[\sqrt{\frac{\varepsilon_{eff}\varepsilon_{metal}}{\varepsilon_{eff} + \varepsilon_{metal}}}\right] \quad \text{equation (3)}$$

Here, Re[ ] represents using the real part within the brackets [ ].

Accordingly, the effective dielectric constant $\varepsilon_{effin}$ of the incident-side portion with respect to plasmon-excitation layer 8 and the effective dielectric constant $\varepsilon_{effout}$ of the emission-side portion are determined by calculation using Equation (1), Equation (2), and Equation (3) and substituting the dielectric constant distribution $\varepsilon_{in}(\omega, x, y, z)$ of the incident-side portion of plasmon-excitation layer 8 and the dielectric constant distribution $\varepsilon_{out}(\omega, x, y, z)$ of the emission-side portion of plasmon-excitation layer 8 as $\varepsilon(\omega, x, y, z)$. In actuality, the effective dielectric constant $\varepsilon_{eff}$ is easily found by giving a suitable initial value as the effective dielectric constant $\varepsilon_{eff}$ and then repeatedly calculating Equation (1), Equation (2), and Equation (3). When the dielectric constant of the layer that makes contact with plasmon-excitation layer 8 is extremely high, the z-component $k_{spp,z}$ of the wave number of the surface plasmons at this interface is a real number. This corresponds to a case in which surface plasmons are not generated at this interface. As a result, the dielectric constant of the layer that makes contact with plasmon-excitation layer 8 corresponds to the effective dielectric constant in this case.

If the effective interactive distance of surface plasmons is the distance at which the intensity of surface plasmons becomes $e^{-2}$, the effective interactive distance $d_{eff}$ of surface plasmons is expressed by:

$$d_{eff} = \text{Im}\left[\frac{1}{k_{spp,z}}\right] \quad \text{equation (4)}$$

Low dielectric constant layer 7 is a layer in which the dielectric constant is lower than that of high dielectric constant layer 9A and high dielectric constant layer 9B. The complex dielectric constant of low dielectric constant layer 7 is $\varepsilon_l(\lambda_0)$, the real part being $\varepsilon_{lr}(\lambda_0)$ and the imaginary part being $\varepsilon_{li}(\lambda 0)$. Further, if the complex dielectric constants of each of high dielectric constant layer 9A and high dielectric constant layer 9B are assumed to be $\varepsilon_{hA}(\lambda_0)$ and $\varepsilon_{hB}(\lambda_0)$, respectively, the real parts of each are assumed to be $\varepsilon_{hrA}(\lambda_0)$ and $\varepsilon_{hrB}(\lambda_0)$, respectively, and the imaginary parts of each are assumed to be $\varepsilon_{hiA}(\lambda_0)$ and $\varepsilon_{hiB}(\lambda_0)$, then the following relational expression will be satisfied.

$$1 \le \varepsilon_{lrA}(\lambda_0) < \varepsilon_{hrA}(\lambda_0) \text{ and } 1 \le \varepsilon_{lrB}(\lambda_0) < \varepsilon_{hrB}(\lambda_0)$$

$\lambda_0$ is the wavelength in a vacuum of incident light to a dielectric constant layer.

However, even when the dielectric constant of low dielectric constant layer 7 is higher than either or both of high dielectric constant layer 9A and high dielectric constant layer 9B, optical element 51 will operate if the real part of the effective dielectric constant of the incident-side portion of plasmon-excitation layer 8 is lower than the real part of the effective dielectric constant of the emission-side portion of plasmon-excitation layer 8. In other words, the dielectric constants of low dielectric constant layer 7, high dielectric constant layer 9A, and high dielectric constant layer 9B are allowed a range within which the real part of the effective dielectric constant of the emission side of plasmon-excitation layer 8 is kept higher than the real part of the effective dielectric constant of the incident side.

In addition, the imaginary part $\varepsilon_{li}(\lambda_0)$ and the imaginary part $\varepsilon_{hi}(\lambda_0)$ in the light emission frequency are preferably as low as possible, thereby facilitating plasmon coupling and enabling a reduction of light loss.

The imaginary part of the complex dielectric constant in the light emission wavelength of carrier-generating layer 6 is preferably as low as possible in every layer except for carrier-generating layer 6, including light guide body 2 and the medium that makes contact with wave vector conversion layer 10. Making the imaginary part of the complex dielectric constant as low as possible facilitates the occurrence of plasmon coupling and enables a reduction of light loss.

The medium of light source apparatus 50, i.e., the medium that contacts light guide body 2 or wave vector conversion layer 10 may include any from among a solid, liquid or gas, and the mediums may differ for the light guide body 2-side and wave vector conversion layer 10-side.

In the present exemplary embodiment, the plurality of light-emitting elements 1a-1n are arranged on the four side surfaces of planar light guide body 2 with predetermined spacing between adjacent elements. It is here assumed that the points at which light-emitting elements 1a-1n makes contact with the side surfaces are light-incident parts 4a. The components that are used as light-emitting elements 1 are, for example, super-luminescent diodes, laser diodes, or light-emitting diodes (LEDs) that emit light of a wavelength that can be absorbed by carrier-generating layer 6. Light-emitting elements 1 may be arranged separated from light-incident parts 4 of light guide body 2, or may be placed in optical contact with light guide body 2 by means of light guide members such as light pipes.

Although light guide body 2 is formed as a planar shape in the exemplary embodiment, the shape of light guide body 2 is not limited to a rectangular parallelepiped. A structure that controls light distribution characteristics such as a microprism may be provided in the interior of light guide body 2. Alternatively, light guide body 2 may be provided with a reflective film on a portion of the outer surface or on all of the outer surfaces other than light-emission part 5 and light-incident part 4. Similarly, light source apparatus 50 may be provided with a reflective film (not shown) on a portion or on all of the outer surfaces other than light-emission part 5 or light-incident part 4. A metal layer such as silver or aluminum or a dielectric multilayer film may be used as the reflective film.

Light guide body 2 is not an indispensible constituent element, and instead of light guide body 2, the light-emission surfaces of light-emitting elements may be arranged in proximity to carrier-generating layer 6.

Figure 4B:
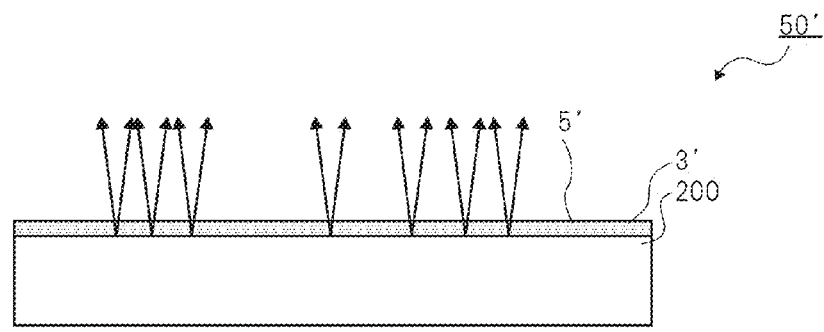
FIG. 4B is a sectional view for describing the behavior of light in a modification of the light source apparatus of the first exemplary embodiment of the present invention.

In addition, light-emitting elements alone may be used in place of light guide body 2 and light-emitting elements 11. FIG. 4B is a sectional view showing, as a modification of this exemplary embodiment, light source apparatus 50' that is provided with directivity control layer 3' on LED 200 that is the light-emitting element. At this time, directivity control layer 3' is arranged on the light-emission surface of LED 200. Directivity control layer 3' and the light-emission surface (not shown) of LED 200 may be arranged at a predetermined spacing through the use of support columns (not shown). Directivity control layer 3' may be arranged so as to contact the light-emission surface (not shown) of LED 200. The construction of directivity control layer 3' is the same as that of directivity control layer 3 shown in FIG. 4A. In the example shown in FIG. 4B, the interface between low dielectric constant layer 7 that constitutes directivity control layer 3' and LED 200 is the light-incident surface. In this modification, light that is emitted from light-emission part 5' is the same as light that is emitted from light-emission part 5 shown in FIG. 4A.

A fluorescent material such as an organic fluorescent material, for example, rhodamine 6G or sulforhodamine 101 and a quantum-dot fluorescent material such as CdSe or CdSe/ZnS quantum dots, an inorganic material (semiconductor) such as GaN or GaAs, or an organic material (semiconductor material) such as (thiophene/phenylene) co-oligomer or Alq3 is used as carrier-generating layer 6. When a fluorescent material is used, a material that gives off fluorescent light in which the emitted light wavelength is the same wavelength or is a plurality of different wavelengths may be mixed in carrier-generating layer 6. The thickness of carrier-generating layer 6 is preferably equal to or less than 1 μm.

Materials that are preferably used as low dielectric constant layer 7 include $SiO_2$ nanorod array film, a thin-film or porous film of $SiO_2$, $AlF_3$, $MgF_2$, $Na_3AlF_6$, NaF, LiF, $CaF_2$, $BaF_2$ or a low-dielectric constant plastic, or an inert gas such as nitrogen or argon.

Materials that are preferably used as high dielectric constant layers 9A and 9B include, for example, high-dielectric constant materials such as diamond, $TiO_2$, $CeO_2$, $Ta_2O_5$, $ZrO_2$, $Sb_2O_3$, $HfO_2$, $La_2O_3$, $NdO_3$, $Y_2O_3$, ZnO, and $Nb_2O_5$.

Plasmon-excitation layer 8 is a microparticle layer or thin-film layer formed by a material having a plasma frequency that is higher than the frequency (emission frequency) of light that is generated when a single carrier-generating layer 6 is excited by the light of light-emitting element 1. In other words, plasmon-excitation layer 8 has a negative dielectric constant in the emission frequency that is generated when a single carrier-generating layer 6 is excited by the light of light-emitting element 1.

Materials that can be used as the material of plasmon-excitation layer 8 include gold, silver, copper, platinum, palladium, rhodium, osmium, ruthenium, iridium, iron, tin, zinc, cobalt, nickel, chromium, titanium, tantalum, tungsten, indium, aluminum, or an alloy of these metals. Of these metals, gold, silver, copper, platinum, aluminum, or an alloy that uses these metals as a principal component is preferably used as the material of plasmon-excitation layer 8, and in particular, gold, silver, aluminum, or an alloy that uses these metals as a principal component is preferably used.

The thickness of plasmon-excitation layer 8 is preferably formed to 200 nm or less, and in particular, is more preferably formed in the order of 10 nm-100 nm. The distance from the interface of high dielectric constant layer 9A and plasmon-excitation layer 8 to the interface of low dielectric constant layer 7 and carrier-generating layer 6 is preferably formed to be 500 nm or less. This distance corresponds to the distance at which plasmon coupling occurs between carrier-generating layer 6 and plasmon-excitation layer 8.

Wave vector conversion layer 10 is an emission layer for extracting light from high dielectric constant layer 9A by converting the wave vector of incident light that is irradiated into this wave vector conversion layer 10 and emitting the light from optical element 51. In other words, wave vector conversion layer 10 converts the emission angle of light from high dielectric constant layer 9A to a predetermined angle and emits the light from optical element 51. Essentially, wave vector conversion layer 10 features the capability of emitting the light emitted from optical element 51 such that the light is substantially orthogonal to the interface with high dielectric constant layer 9A.

Examples of components that are used as wave vector conversion layer 10 include a surface relief grating, a periodic structure in which photonic crystal is representative, a semi-periodic structure (a structure with texture greater than the wavelength of light from high dielectric constant layer 9A) or semi-crystalline structure, a surface structure on which a rough surface is formed, a hologram, and a microlens array. A semi-periodic structure refers to a periodic structure that is not complete (not perfect) in which, for example, a portion of the periodic structure is lacking. Of these structures, a periodic structure of which a photonic crystal is representative, a semi-periodic structure, a semi-crystalline structure, and a microlens array are preferably used. The reason for this preference is not only the increased light extraction efficiency but also the capability to control directivity. In addition, when photonic crystal is used, the crystalline structure preferably takes on the shape of a triangular grating structure. A structure in which protrusions are provided on a planar base may also be used as wave vector conversion layer 10. Still further, wave vector conversion layer 10 may be constituted by a material that differs from high dielectric constant layer 9A.

The dielectric constant of low dielectric constant layer 7 that is arranged directly below carrier-generating layer 6 may be set lower than the dielectric constant of light guide body 2. In this case, the angle of incidence with respect to light-incident part 4 of light guide body 2 is set to a predetermined angle such that incident light from light-emitting element 1 undergoes total reflection at the interface of light guide body 2 and low dielectric constant layer 7.

The incident light that is irradiated into light guide body 2 from light-emitting element 1 undergoes total reflection at the interface of light guide body 2 and low dielectric constant layer 7, and evanescent waves are generated together with this total reflection. These evanescent waves act upon carrier-generating layer 6 to generate carriers in carrier-generating layer 6.

Generating carriers by only evanescent waves, as in the present exemplary embodiment, enables the decrease of, of the light emitted from light source apparatus 50, light that corresponds to the emission wavelength of light-emitting element 1 and the increase of light that corresponds to the emission wavelength of carrier-generating layer 6. Accordingly, the utilization efficiency of light from light-emitting element 1 can be increased.

The dielectric constant of low dielectric constant layer 7 that is arranged directly below carrier-generating layer 6 may be higher than the dielectric constant of light guide body 2, and the incident light from light-emitting element 1 may be set to be incident at an angle so as not to undergo total reflection at the interface of light guide body 2 and low dielectric constant layer 7.

In the present exemplary embodiment, moreover, high dielectric constant layer 9B is formed between carrier-generating layer 6 and plasmon-excitation layer 8. The purpose of this configuration is to improve the efficiency of plasmon coupling between carrier-generating layer 6 and plasmon-excitation layer 8.

The operations by which light that is incident to directivity control layer 3 from light-emitting element 1 and that is emitted from light-emission part 5 of directivity control layer 3 are next described for light source apparatus 50 that is configured as described hereinabove.

As shown in FIG. 4A, light that is emitted from among the plurality of light-emitting elements 1, such as, for example, light-emitting element if is transmitted through light-incident part 4a of light guide body 2 and propagated while undergoing total reflection within light guide body 2. At this time, a portion of the light that was incident to the interface of light guide body 2 and directivity control layer 3 is emitted from light-emission part 5 in a direction and wavelength that accord with characteristics (to be described hereinbelow) in plasmon-excitation layer 8 of directivity control layer 3. The light that is not emitted from light-emission part 5 is returned to light guide body 2, and again, a portion of the light that was incident to the interface of light guide body 2 and directivity control layer 3 is transmitted through directivity control layer 3 and emitted from light-emission part 5. Through the repetition of these actions, most of the light that is incident to light guide body 2 is emitted from light-emission part 5. In addition, light that is emitted from, from among the plurality of light-emitting elements 1, light-emitting element 1m that is arranged at position opposite light-emitting element if with light guide body 2 interposed, and that is transmitted through light-incident part 4b is similarly emitted from light-emission part 5. The direction and wavelength of light that is emitted from light-emission part 5 depend only on the characteristics of directivity control layer 3 and do not depend on the position of light-emitting element 1 or the angle of incidence to the interface of light guide body 2 and directivity control layer 3. The following explanation regards a case in which the wave vector conversion layer is a photonic crystal unless specifically stated. If surfaces other than light-incident part 4 of light guide body 2 are reflecting surfaces or scattering surfaces, light that is irradiated into light guide body 2 need not undergo total reflection.

FIGS. 5A and 5B are enlarged views for describing the configuration and function of directivity control layer 3. In light that is propagated by total reflection inside light guide body 2, the conditions for total reflection break down at the interface of light guide body 2 and low dielectric constant layer 7, whereby light from light-emitting element 1 passes through low dielectric constant layer 7 to be irradiated into carrier-generating layer 6. The light that is irradiated into carrier-generating layer 6 generates carriers in carrier-generating layer 6. The generated carriers bring about plasmon coupling with free electrons in plasmon-excitation layer 8. Radiation into high dielectric constant layer 9A is brought about by way of this plasmon coupling, and this light is diffracted at wave vector conversion layer 10 and emitted from light source apparatus 50. The light that is emitted from one point of high dielectric constant layer 9A has a ring-shaped intensity distribution that spreads in the shape of a concentric circle as it is propagated. If the emission angle at which the intensity is highest is the central emission angle and if the angular width from the central emission angle to the emission angle at which the intensity is halved is the emission angle width, the central emission angle and the emission angle width of light that is emitted from high dielectric constant layer 9A are determined by the effective dielectric constant of the emission-side portion and incident-side portion of plasmon-excitation layer 8, the complex dielectric constant of plasmon-excitation layer 8, and the emission spectral band width of carrier-generating layer 6.

Figure 5C:
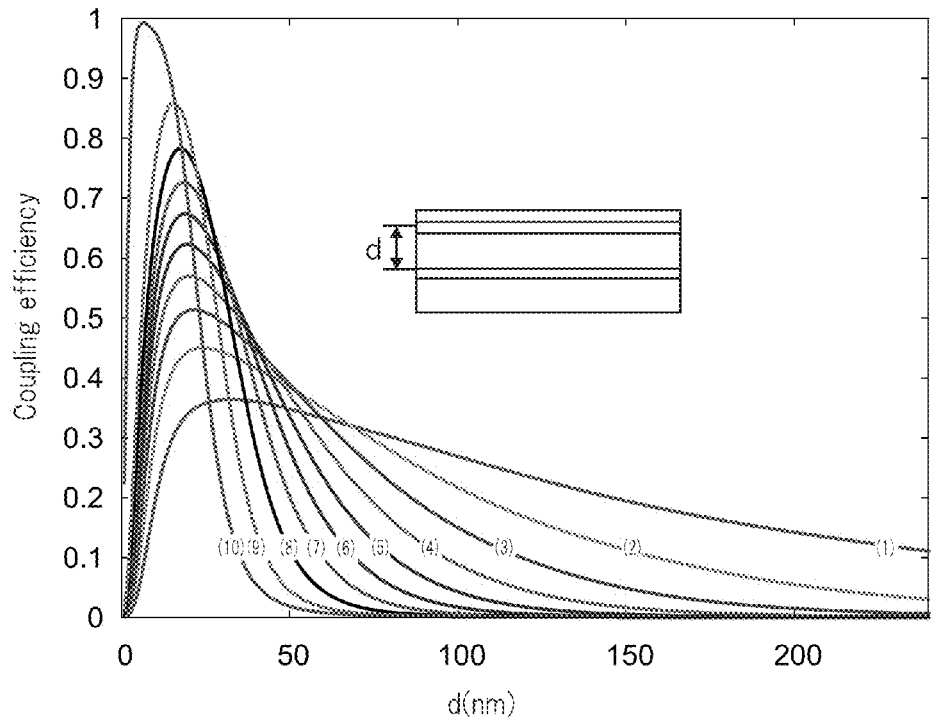
FIG. 5C shows the plasmon coupling efficiency of a fluorescent layer and metal layer of the first exemplary embodiment.

FIG. 5C shows the plasmon coupling efficiency between a fluorescent layer and metal layer when the spacing between the point of light emission in a fluorescent layer that is used as carrier-generating layer 6 and metal layer that is used as plasmon-excitation layer 8 is d and the dielectric constant of the layer that is provided between these layers is made from 1 to 10. Here, the dielectric constant of carrier-generating layer 6 is made the same as the dielectric constant between the fluorescent layer and metal layer. As shown in the figure, it can be understood that the efficiency of plasmon coupling increases as the dielectric constant between the fluorescent layer and metal layer increases.

In the present exemplary embodiment, as described hereinabove, the efficiency of plasmon coupling between carrier-generating layer 6 and plasmon-excitation layer 8 is improved by forming high dielectric constant layer 9B between carrier-generating layer 6 and plasmon-excitation layer 8, and in addition, the occurrence of plasmon coupling is further facilitated by forming low dielectric constant layer 7 in the portion on light guide body 2-side from carrier-generating layer 6.

Figure 5D:
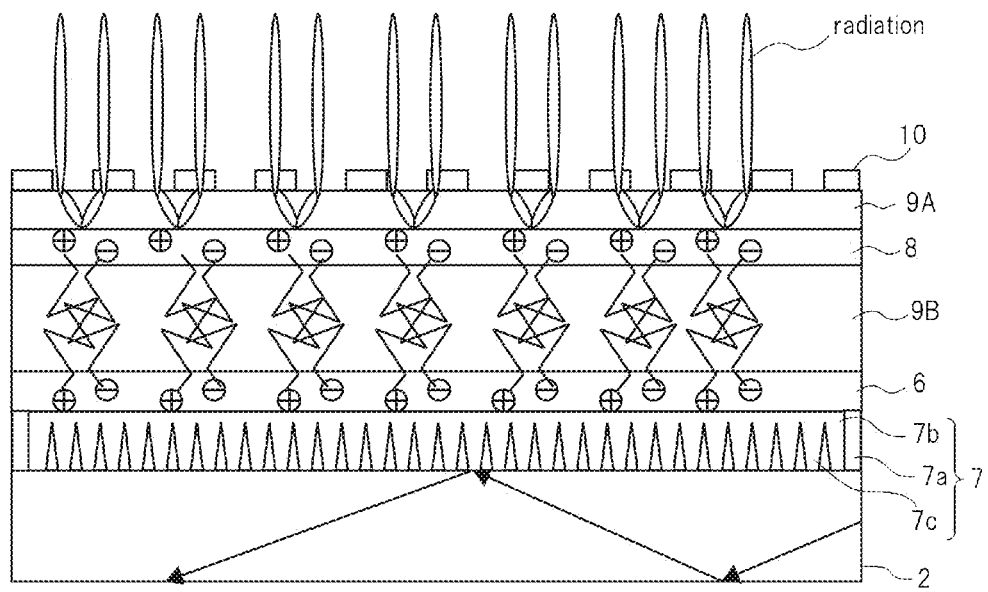
FIG. 5D shows the configuration of an example in which gas is used as the low-dielectric layer of the first exemplary embodiment.

FIG. 5D shows the configuration of an example that uses gas as the low dielectric constant layer.

Low dielectric constant layer 7' shown in FIG. 5D is realized by gap 7b that is filled by an inert gas and hermetically sealed by columns 7a, and light-extraction structure 7c in which a plurality of spikes are arranged periodically is formed inside.

Figure 5E:
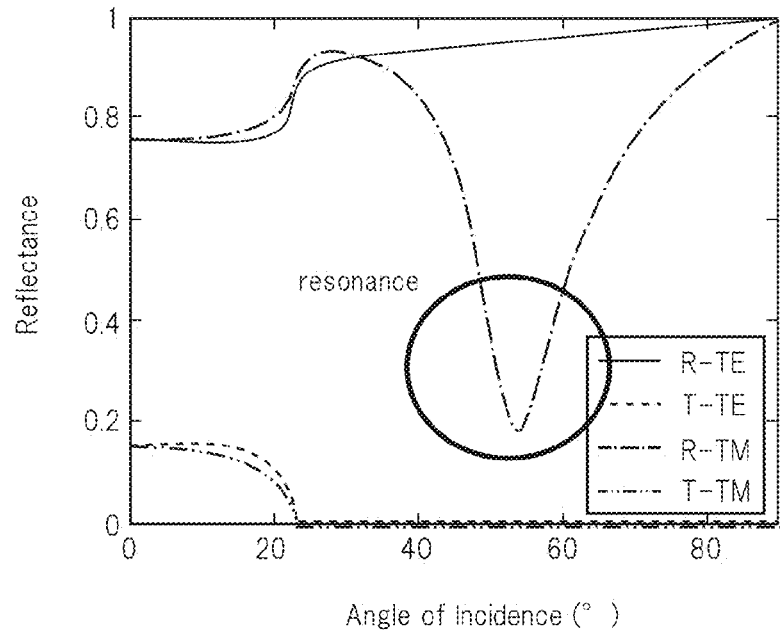
FIG. 5E shows the result of simulating the reflectance for angles of incidence with respect to carrier-generating layer 6 shown in FIG. 5D.
Figure 5F:
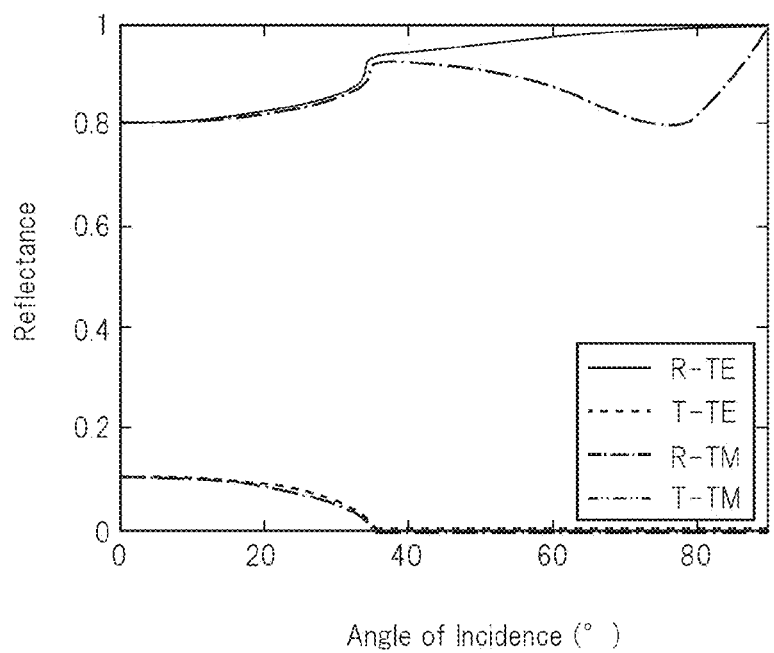
FIG. 5F shows the result of the simulating reflectance for angles of incidence to carrier-generating layer 6 in which there is no gap in the element.

FIG. 5E shows the results of simulating reflectance with respect to the angle of incidence to carrier-generating layer 6 shown in FIG. 5D when the dielectric constant of high dielectric constant layer 9A is raised to further increase efficiency. Here, $TiO_2$ is used for wave vector conversion layer 10, $TiO_2$ having an infinite thickness is used for high dielectric constant layer 9A, Ag having a thickness of 50 nm is used for plasmon-excitation layer 8, $TiO_2$ having a thickness of 10 nm is used for high dielectric constant layer 9A, quantum dots having a thickness of 25 nm are used for carrier-generating layer 6, and the emission wavelength of the fluorescent material is made to be 530 nm. In addition, light guide body 2 is assumed to be PMMA of infinite thickness. FIG. 5F shows the result of simulating reflectance with respect to the angle of incidence to carrier-generating layer 6 when there is no gap, as a comparative example.

In both FIG. 5E and FIG. 5F, the solid lines represent the reflectance of the reflected light of TE waves, the alternate long and short dash lines represent the reflectance of reflected light of TM waves, the dotted lines represent the reflectance of the transmitted light of TE waves, and the alternate long and two short dashes lines represent the reflectance of the transmitted light of TM waves.

As shown in FIG. 5E, when low dielectric constant layer 7' is provided, the plasmon resonance conditions are satisfied and reflectance undergoes a steep drop in the vicinity of an angle of incidence of 57°.

Figure 6:
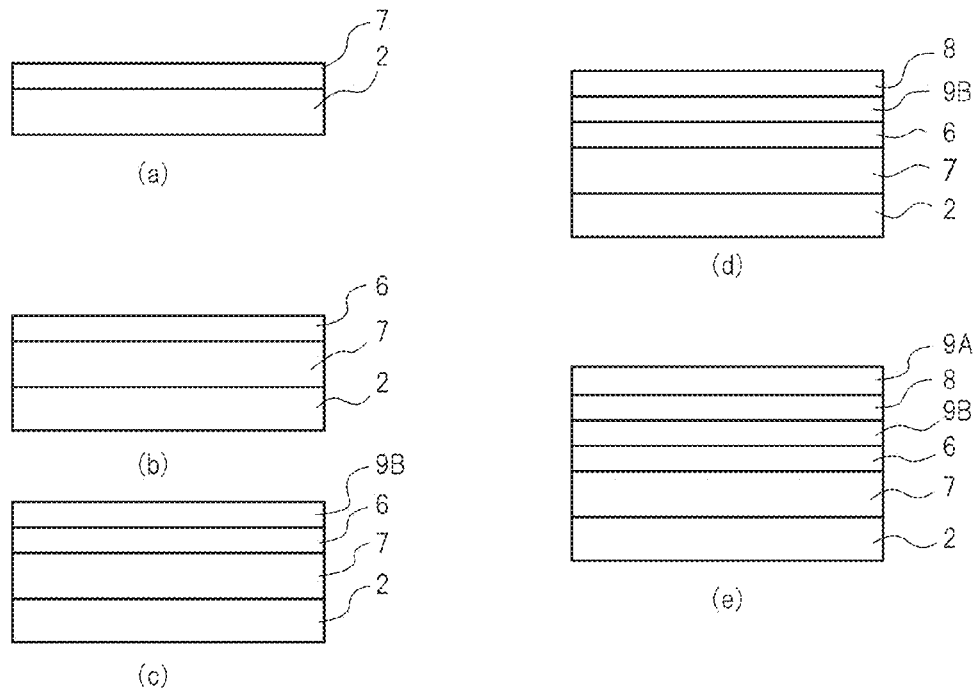
FIG. 6 (a)-(e) are sectional views for describing the fabrication steps in the light source apparatus of the first exemplary embodiment.

FIG. 6 shows the fabrication steps of optical element 51 that is provided in light source apparatus 50. These fabrication steps are only an example, and the present invention is not limited to this fabrication method. First, as shown in FIG. 6(a), low dielectric constant layer 7 is formed on light guide body 2, following which carrier-generating layer 6 is applied to low dielectric constant layer 7 by means of a spin-coating method as shown in FIG. 6(b). Next, as shown in FIG. 6(c) to FIG. 6(e), high dielectric constant layer 9B, plasmon-excitation layer 8, and high dielectric constant layer 9A are successively stacked on carrier-generating layer 6 by means of, for example, physical vapor deposition, electron beam evaporation, or sputtering.

Figure 7:
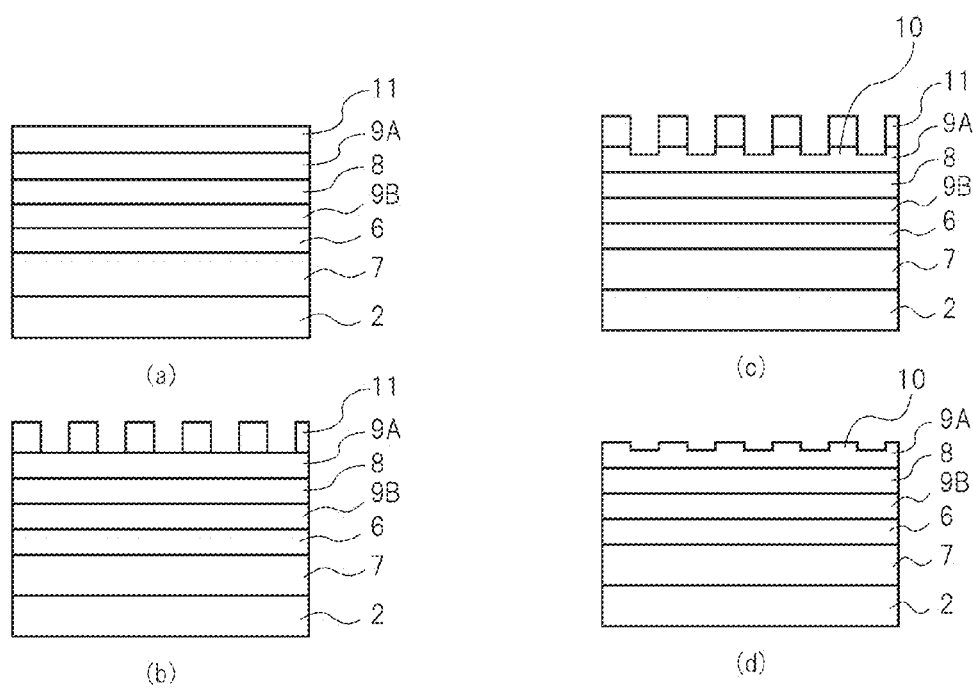
FIG. 7 (a)-(d) are sectional views for describing the formation steps of the photonic crystal in the light source apparatus of the first exemplary embodiment.

FIG. 7 shows fabrication steps by which wave vector conversion layer 10 is formed of photonic crystal. As shown in FIG. 7(a), wave vector conversion layer 10 is formed on high dielectric constant layer 9A, resist film 11 is applied over this wave vector conversion layer 10 by a spin-coat method, and then, as shown in FIG. 7(b), a negative pattern of the photonic crystal is transferred onto resist film 11 by nano-imprinting. Wave vector conversion layer 10 is next etched to the desired depth by a dry etching method as shown in FIG. 7(c), following which resist film 11 is removed as shown in FIG. 7(d). Finally, light source apparatus 50 is completed by arranging a plurality of light-emitting elements 1 on the outer periphery of light guide body 2.

Figure 8:
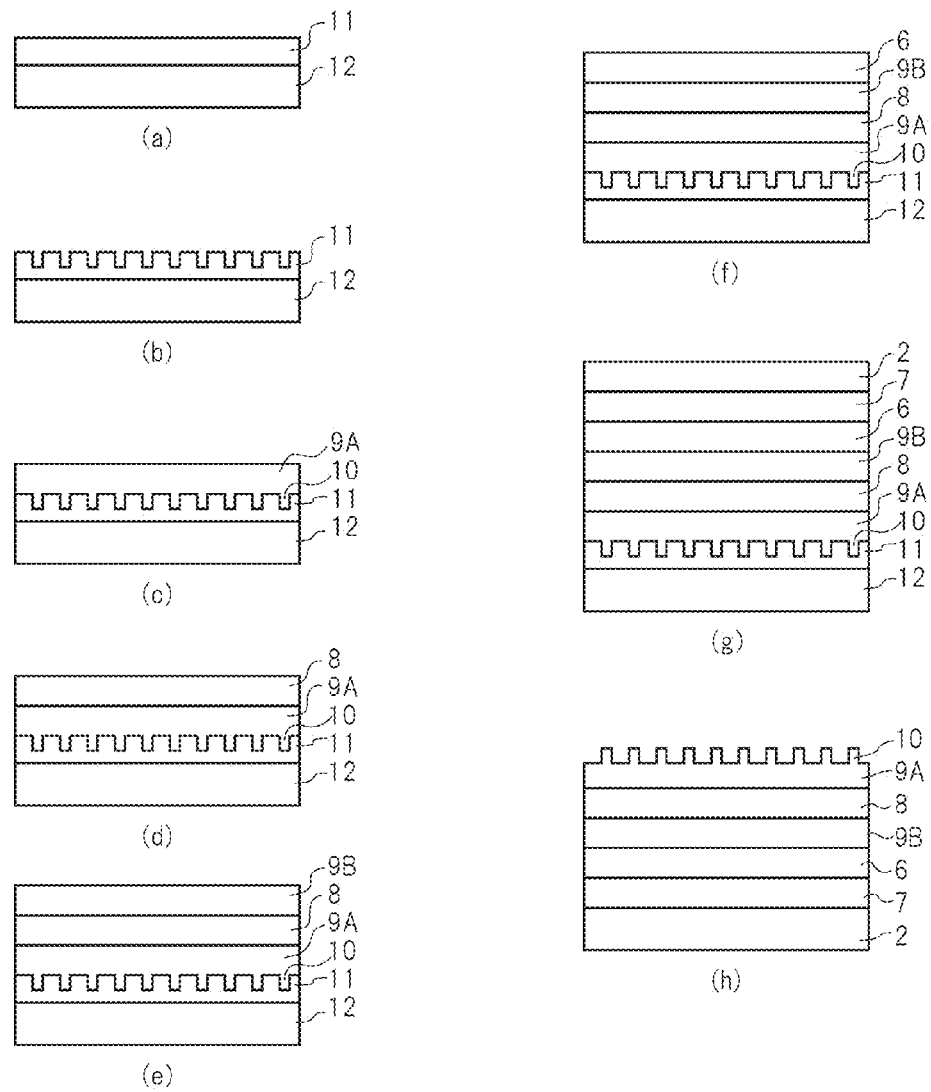
FIG. 8 (a)-(h) are sectional views for describing another example of the formation steps of the photonic crystal in the light source apparatus of the first exemplary embodiment.

FIG. 8 shows other fabrication steps for forming wave vector conversion layer 10 by means of photonic crystal formed on the surface of high dielectric constant layer 9 of light source apparatus 50. These steps are for illustrative purposes only, and the present invention is not limited to these fabrication methods.

First, as shown in FIG. 8(a), resist film 11 is applied to substrate 12 by a spin-coat method, following which a negative pattern of a photonic crystal is transferred to resist film 11 by nano-imprinting as shown in FIG. 8(b). High dielectric constant layer 9A, plasmon-excitation layer 8, and high dielectric constant layer 9B are next successively laminated by means of physical vapor deposition, electron beam vapor deposition, or sputtering as shown in FIG. 8(c) to FIG. 8(e). Next, as shown in FIG. 8(f), carrier-generating layer 6 is applied to high dielectric constant layer 9B by a spin-coat method, following which, as shown in FIG. 8(g), low dielectric constant layer 7 is formed by physical vapor deposition, electron beam vapor deposition, or sputtering and light guide body 2 is pressure-bonded to low dielectric constant layer 7 and dried. Finally, resist film 11 is removed from substrate 12 as shown in FIG. 8(h), following which light source apparatus 50 is completed by arranging a plurality of light-emitting elements 1 on the outer periphery of light guide body 2.

The surface of high dielectric constant layer 9A that is on the side opposite to light guide body 2 may be a structure in which, instead of using photonic crystal as wave vector conversion layer 10, a microlens array is arranged or a configuration in which a rough surface is formed.

Figure 9:
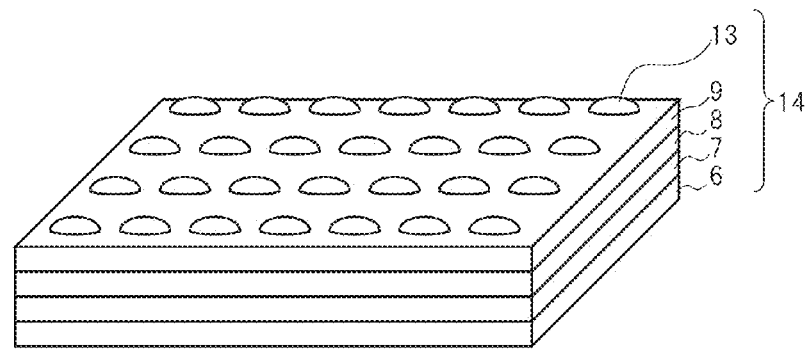
FIG. 9 is a perspective view showing the configuration in which a microlens array is provided on the surface of the directivity control layer in the first exemplary embodiment.

FIG. 9 shows an example of the configuration of the directivity control layer in which a microlens array is provided on the surface of high dielectric constant layer 9. Even when directivity control layer 14 is a configuration equipped with microlens array 13 as shown in FIG. 9, the same effect is obtained as when photonic crystal is used as wave vector conversion layer 10.

Figure 10:
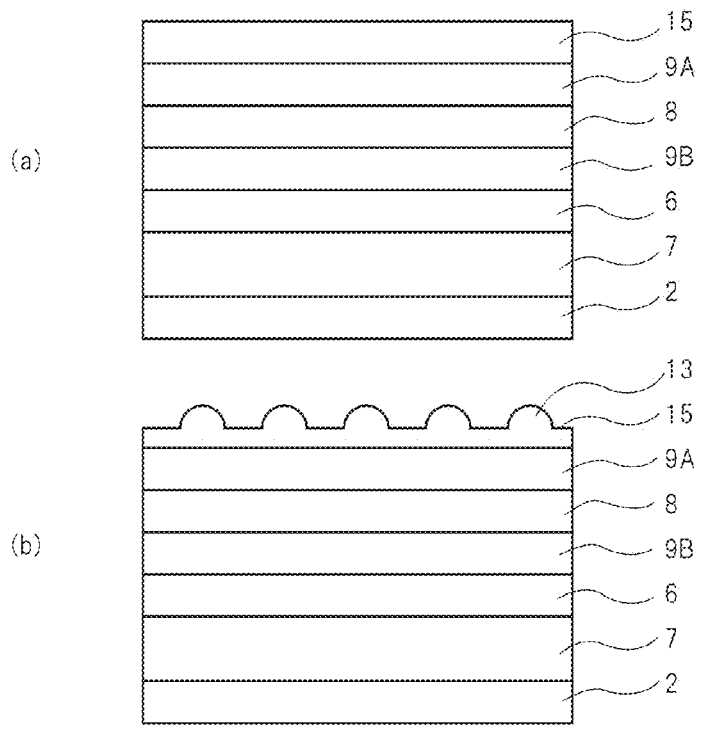
FIGS. 10 (a)-(b) are sectional views for describing the formation steps of the microlens array in the light source apparatus of the first exemplary embodiment.

FIG. 10(a) and FIG. 10(b) are sectional views for describing the fabrication steps of a configuration in which microlens array 13 is laminated on high dielectric constant layer 9A. In the configuration provided with microlens array 13, each of the layers from carrier-generating layer 6 to high dielectric constant layer 9A are stacked on light guide body 2 similar to the fabrication method shown in FIG. 6(a) to FIG. 6(e), and explanation of these fabrication steps is therefore here omitted.

As shown in FIG. 10(a) and FIG. 10(b), after depositing each of the layers from carrier-generating layer 6 to high dielectric constant layer 9A on light guide body 2 using the fabrication method shown in FIG. 6(a) to FIG. 6(e), microlens array 13 is formed on the surface of high dielectric constant layer 9A. This is for illustrative purposes only, and the present invention is not limited to this fabrication method. After applying UV-curing resin 15 onto the surface of high dielectric constant layer 9A by a method such as spin-coating, a desired lens array pattern is formed on UV-curing resin 15 using nano-imprinting, following which microlens array 13 is formed by irradiating light upon UV-curing resin 15 to cure the resin.

Light source apparatus 50 of the present exemplary embodiment as described hereinabove is able to realize a miniaturization of light source apparatus 50 overall due to the comparatively simple configuration in which directivity control layer 3 is provided on light guide body 2. In addition, by means of light source apparatus 50 of the present exemplary embodiment, the angle of incidence of light that is irradiated into wave vector conversion layer 10 is determined only by the dielectric constants of plasmon-excitation layer 8 and low dielectric constant layer 7 and high dielectric constant layer 9A that sandwich this plasmon-excitation layer 8. As a result, the directivity of light emitted from optical element 51 is no longer limited by the directivity of light-emitting elements 1. In addition, light source apparatus 50 of the present exemplary embodiment, by applying plasmon coupling in the radiation process, is able to narrow the angle of radiation of light emitted from optical element 51 and thus raise the directivity of light emitted. In other words, according to the present exemplary embodiment, the etendue of emitted light from optical element 51 can be reduced without needing to depend on the etendue of light-emitting elements 1. In addition, because the etendue of emitted light from light source apparatus 50 is not limited by the etendue of light-emitting elements 1, irradiated light from a plurality of light-emitting elements 1 can be synthesized while keeping the etendue of light emitted from light source apparatus 50 at a low level.

In addition, in the configuration that was disclosed in the above-described Patent Document 1, the problem arose that the size of the overall light source unit was increased due to the provision of axis parts 82a-82d and light source sets 81a and 81b. However, optical element 51 of the present exemplary embodiment e enables realizing an overall smaller optical element 51.

The configuration disclosed in the above-described Patent Document 2 entailed the problem of loss of light due to the bending of light from a plurality of LEDs 85 in various directions by crossing prism sheets 88 and 89. However, optical element 51 of the present exemplary embodiment enables improving of the utilization efficiency of light emitted from a plurality of light-emitting elements 1.

Light source apparatuses of other exemplary embodiments are described hereinbelow. The light source apparatuses of other exemplary embodiments differ from light source apparatus 50 of the first exemplary embodiment only with regard to the configuration of directivity control layer 3, and explanation therefore relates only to directivity control layer 3. In the directivity control layers of the other exemplary embodiments, layers that are identical to those of directivity control layer 3 in the first exemplary embodiment are given the same reference numbers as in the first exemplary embodiment and redundant explanation is omitted.

In addition, although configurations are shown in the following exemplary embodiments in which wave vector conversion layer 10 is composed of photonic crystal, wave vector conversion layer 10 may be replaced by the above-described microlens array 13 and similar effects will be obtained.

Although explanation is presented using low dielectric constant layer 7 shown in FIG. 5B as the low dielectric constant layer, low dielectric constant layer 7' shown in FIG. 5D acts in the same manner. As a result, low dielectric constant layer 7' may, of course, be used in each of the following exemplary embodiments, and the present invention includes embodiments in which low dielectric constant layer 7' is used in each of the following exemplary embodiments.

Second Exemplary Embodiment

Figure 11:
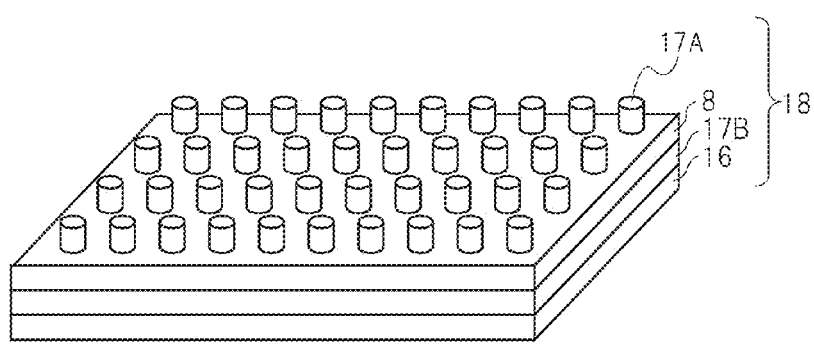
FIG. 11 is a schematic perspective view of the directivity control layer provided in the light source apparatus of the second exemplary embodiment.

FIG. 11 shows a perspective view of the directivity control layer that is provided in the light source apparatus of the second exemplary embodiment. As shown in FIG. 11, in directivity control layer 18 in the second exemplary embodiment, carrier-generating layer 16, high dielectric constant layer 17B, plasmon-excitation layer 8, and wave vector conversion layer 17A that is composed of photonic crystal are stacked in that order on a light guide body (not shown in the figure).

In directivity control layer 18 in the second exemplary embodiment, wave vector conversion layer 17A also serves as high dielectric constant layer 9A in the first exemplary embodiment, carrier-generating layer 16 also serves as low dielectric constant layer 7 in the first exemplary embodiment, and the interface of carrier-generating layer 16 and the light guide is the incident surface. Accordingly, in order to induce plasmon coupling in plasmon-excitation layer 8, the dielectric constant of wave vector conversion layer 17A, which is the layer arranged adjacent to the emission-side interface of plasmon-excitation layer 8, is set higher than the dielectric constant of carrier-generating layer 16, which is the layer arranged on the incident-side interface of plasmon-excitation layer 8 with high dielectric constant layer 17B interposed therebetween. However, directivity control layer 18 will operate even when the dielectric constant of wave vector conversion layer 17A is lower than the dielectric constant of carrier-generating layer 16, as long as the real part of the effective dielectric constant of the wave vector conversion layer 17A-side of plasmon-excitation layer 8 is higher than the real part of the effective dielectric constant of the carrier-generating layer 16-side of plasmon-excitation layer 8. In other words, the dielectric constant of wave vector conversion layer 17A is permitted a range in which the real part of the effective dielectric constant of the emission-side portion of plasmon-excitation layer 8 is kept higher than the real part of the effective dielectric constant of the incident-side portion of plasmon-excitation layer 8.

According to the light source apparatus of the second exemplary embodiment that is configured as described above, not only can the same effects be obtained as in the first exemplary embodiment, but a further reduction in size compared to the first exemplary embodiment can also be achieved.

Third Exemplary Embodiment

Figure 12:
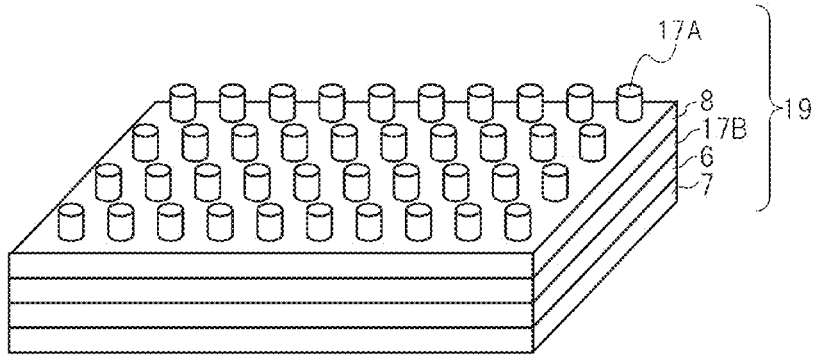
FIG. 12 is a schematic perspective view of the directivity control layer provided in the light source apparatus of the third exemplary embodiment.

FIG. 12 shows a perspective view of the directivity control layer that is provided in the light source apparatus of the third exemplary embodiment. As shown in FIG. 12, in directivity control layer 19 in the third exemplary embodiment, low dielectric constant layer 7, carrier-generating layer 6, high dielectric constant layer 17B, plasmon-excitation layer 8, and wave vector conversion layer 17A composed of photonic crystal are stacked in that order on a light guide body (not shown). In the present exemplary embodiment, the interface of low dielectric constant layer 7 and the light guide body is the incident surface.

In directivity control layer 19 in the third exemplary embodiment, wave vector conversion layer 17A also serves as high dielectric constant layer 9 in the first exemplary embodiment. Thus, in order to induce plasmon coupling in plasmon-excitation layer 8, the dielectric constant of wave vector conversion layer 17A is set higher than the dielectric constant of low dielectric constant layer 7. However, even when the dielectric constant of wave vector conversion layer 17A is lower than the dielectric constant of low dielectric constant layer 7, directivity control layer 19 will operate as long as the real part of the effective dielectric constant of the wave vector conversion layer 17A-side of plasmon-excitation layer 8 is higher than the real part of the effective dielectric constant of the low dielectric constant layer 7-side of plasmon-excitation layer 8. In other words, the dielectric constant of wave vector conversion layer 17A is permitted a range in which the real part of the effective dielectric constant of the emission-side portion of plasmon-excitation layer 8 is kept higher than the real part of the effective dielectric constant of the incident-side portion of plasmon-excitation layer 8.

The light source apparatus of the third exemplary embodiment that is configured as described hereinabove not only obtains the same effects as the first exemplary embodiment, but can also realize an even more compact size than the first exemplary embodiment.

Fourth Exemplary Embodiment

Figure 13:
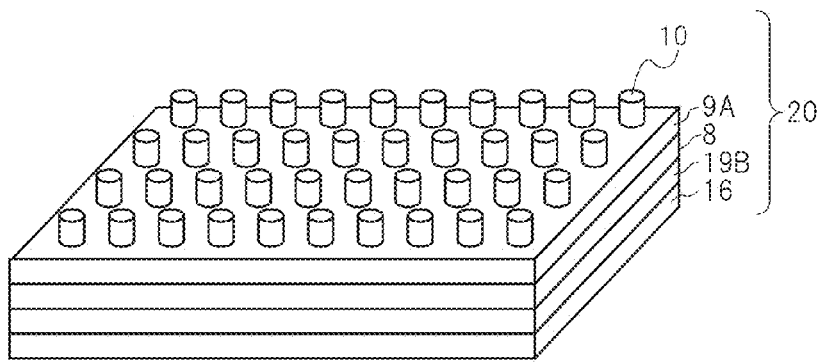
FIG. 13 is a schematic perspective view of the directivity control layer provided in the light source apparatus of the fourth exemplary embodiment.

FIG. 13 is a perspective view of the directivity control layer that is provided in the light source apparatus of the fourth exemplary embodiment. As shown in FIG. 13, in directivity control layer 20 in the fourth exemplary embodiment, carrier-generating layer 16, high dielectric constant layer 9B, plasmon-excitation layer 8, high dielectric constant layer 9A, and wave vector conversion layer 10 composed of photonic crystal are stacked in that order on a light guide body (not shown).

In directivity control layer 20 in the fourth exemplary embodiment, carrier-generating layer 16 also serves as low dielectric constant layer 7 in the first exemplary embodiment, and the interface of carrier-generating layer 16 and the light guide body is the incident surface. Accordingly, in order to induce plasmon coupling in plasmon-excitation layer 8, the dielectric constant of carrier-generating layer 16 is set lower than that of high dielectric constant layer 9A. However, even when the dielectric constant of carrier-generating layer 16 is higher than the dielectric constant of high dielectric constant layer 9A, directivity control layer 20 will operate as long as the real part of the effective dielectric constant of the carrier-generating layer 16-side of plasmon-excitation layer 8 is lower than the real part of the effective dielectric constant of the high dielectric constant layer 9A-side of plasmon-excitation layer 8. In other words, the dielectric constant of carrier-generating layer 16 is permitted a range in which the real part of the effective dielectric constant of the emission-side portion of plasmon-excitation layer 8 is kept higher than the real part of the effective dielectric constant of the incident-side portion of plasmon-excitation layer 8.

The light source apparatus of the fourth exemplary embodiment that is configured as described above not only obtains the same effects as the first exemplary embodiment, but can also enable the realization of an even more compact size than the first exemplary embodiment.

Fifth Exemplary Embodiment

Figure 14:
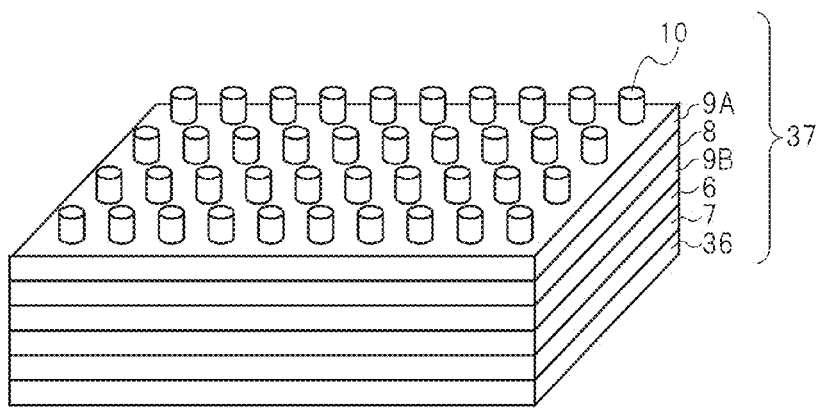
FIG. 14 is a schematic perspective view of the directivity control layer provided in the light source apparatus of the fifth exemplary embodiment.

FIG. 14 shows a perspective view of the directivity control layer that is provided in the light source apparatus of the fifth exemplary embodiment. As shown in FIG. 14, in directivity control layer 37 in the fifth exemplary embodiment, plasmon-excitation layer 36 is further arranged as another plasmon-excitation layer in addition to plasmon-excitation layer 8 in the first exemplary embodiment.

In directivity control layer 37 in the fifth exemplary embodiment, plasmon-excitation layer 36 is arranged between low dielectric constant layer 7 and the light guide body (not shown). In the present exemplary embodiment, the interface of plasmon-excitation layer 36 and the light guide body is the incident surface. In directivity control layer 37, plasmons are excited in plasmon-excitation layer 36 by light that is irradiated from the light guide body and carriers are generated in carrier-generating layer 6 by these excited plasmons.

At this time, the dielectric constant of carrier-generating layer 6 is made lower than the dielectric constant of the light guide body to induce plasmon resonance in plasmon-excitation layer 36. In addition, low dielectric constant layer 7 is provided between plasmon-excitation layer 36 and carrier-generating layer 6 to broaden the range of material selection of carrier-generating layer 6 and the real part of the complex dielectric constant is made lower than that of the light guide body. Here, the effective dielectric constant of the light guide body-side of plasmon-excitation layer 36 must be higher than the effective dielectric constant of the carrier-generating layer 6-side of plasmon-excitation layer 36.

Plasmon-excitation layer 8 has a plasma frequency that is higher than the frequency of light that is generated when single carrier-generating layer 6 is excited by the light of light-emitting element 1. Plasmon-excitation layer 36 has a plasma frequency that is higher than the emission frequency of a light-emitting element (not shown). In addition, when carrier-generating layer 6, that has a plurality of different emission frequencies, is used, plasmon-excitation layer 8 has a plasma frequency that is higher than any of the different frequencies of light that is generated when single carrier-generating layer 6 is exited by the light of light-emitting element 1. Similarly, when a plurality of types of light-emitting elements having different emission frequencies are used, plasmon-excitation layer 36 has a plasma frequency that is higher than any of the different emission frequencies of the light-emitting elements.

Here, in order for light from light-emitting elements to couple with plasmons at the interface of plasmon-excitation layer 36, conditions exist regarding the angle of incidence of light that is irradiated to plasmon-excitation layer 36 from the light-emitting elements. Light must be irradiated at an angle of incidence whereby, from among the wave vectors of incident light on the carrier-generating layer 6-side of plasmon-excitation layer 36, the component that is parallel to the interface matches the component that is parallel to the interface of the surface plasmons on the carrier-generating layer 6-side of plasmon-excitation layer 36.

By means of this configuration, carriers are generated by plasmons in carrier-generating layer 6, whereby a fluorescent intensifying effect due to plasmons can be used.

The fifth exemplary embodiment that is configured as described hereinabove can efficiently generate carriers in carrier-generating layer 6 due to the fluorescent intensifying effect realized by plasmons and thus can increase carriers, whereby the utilization efficiency of light from light-emitting element 1 can be further increased.

Sixth Exemplary Embodiment

Figure 15:
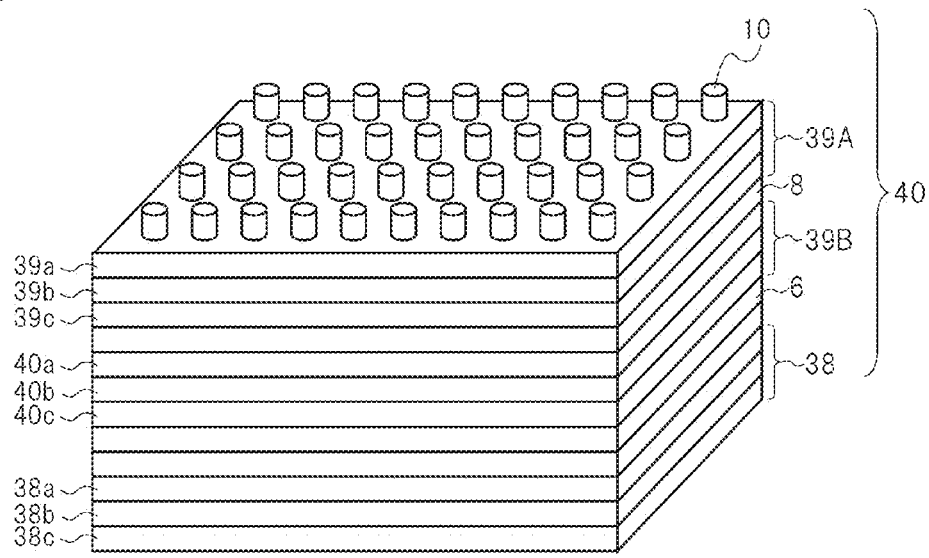
FIG. 15 is a schematic perspective view of the directivity control layer provided in the light source apparatus of the sixth exemplary embodiment.

FIG. 15 shows a perspective view of the directivity control layer that is provided in the light source apparatus of the sixth exemplary embodiment. As shown in FIG. 15, directivity control layer 40 in the sixth exemplary embodiment is of the same configuration as directivity control layer 3 in the first exemplary embodiment, and differs in that low dielectric constant layer 7 and high dielectric constant layers 9A and 9B in the first exemplary embodiment are constituted by a plurality of dielectric layers that are each stacked.

Essentially, directivity control layer 40 in the sixth exemplary embodiment is provided with: low dielectric constant layer group 38 in which a plurality of dielectric layers 38a-38c are stacked, high dielectric constant layer group 39A in which a plurality of dielectric layers 39a-39c are stacked, and high dielectric constant layer group 39B in which a plurality of dielectric layers 40a-40c are stacked. In this exemplary embodiment, the interface of low dielectric constant layer 38c and the light guide body (not shown) is the incident surface.

In low dielectric constant layer group 38, a plurality of dielectric layers 38a-38c is arranged such that the dielectric constant decreases monotonously toward carrier-generating layer 6. Similarly, in high dielectric constant layer group 39B, the plurality of dielectric layers 40a-40c is stacked such that the dielectric constant decreases monotonously toward plasmon-excitation layer 8, and in high dielectric constant layer group 39B, the plurality of dielectric layers 39a-39c is stacked such that the dielectric constant decreases monotonously toward the side of wave vector conversion layer 10 that is made up by photonic crystal.

The overall thickness of low dielectric constant layer group 38 is equal to that of the low dielectric constant layer in exemplary embodiments in which directivity control layer 40 is provided with an independent low dielectric constant layer. Similarly, the overall thicknesses of high dielectric constant layer groups 39A and 39B are the same as the high dielectric constant layers in the exemplary embodiment in which the directivity control layer is provided with high dielectric constant layers independently. Although low dielectric constant layer group 38 and high dielectric constant layer groups 39A and 39B are each shown as three-layer structures, these can also be, for example, structures of from two to five layers. In addition, the low dielectric constant layer group and the high dielectric constant layer groups may be structures in which the number of dielectric layers that make up each group differs, or may be structures in which only the low dielectric constant layer or one of the high dielectric constant layers is composed of a plurality of dielectric layers.

Constructing the high dielectric constant layers and the low dielectric constant layer from a plurality of dielectric layers in this way not only enables appropriate setting of the dielectric constant of each dielectric layer that is adjacent to the interface of plasmon-excitation layer 8, but also enables matching of the index of refraction of carrier-generating layer 6, wave vector conversion layer 10, or a medium such as external air with the dielectric layers that are adjacent to these components. In other words, high dielectric constant layer group 39A can reduce the difference in the indices of refraction at the interface with wave vector conversion layer 10 or a medium such as air; high dielectric constant layer group 39B can reduce the difference in the indices of refraction at the interface with plasmon-excitation layer 8; and low dielectric constant layer group 38 can reduce the difference in the indices of refraction at the interface with carrier-generating layer 6.

According to directivity control layer 40 of the sixth exemplary embodiment that is configured as described hereinabove, not only can the dielectric constant of each dielectric layer that is adjacent to plasmon-excitation layer 8 be suitably set, but the difference in the indices of refraction at the interface with carrier-generating layer 6 and wave vector conversion layer 10 can be set to a low level. As a result, light loss can be further reduced, and the utilization efficiency of light from light-emitting elements can be further increased.

Single-layer films within which the dielectric constant changes monotonously may be used in place of low dielectric constant layer group 38 and high dielectric constant layer groups 39A and 39B. In the case of this configuration, one high dielectric constant layer has a distribution in which the dielectric constant gradually decreases from the plasmon-excitation layer 8-side toward the wave vector conversion layer 10-side, and the other high dielectric constant layer, has a distribution in which the dielectric constant gradually decreases toward plasmon-excitation layer 8. Similarly, the low dielectric constant layer has a distribution in which the dielectric constant gradually decreases toward carrier-generating layer 6.

Seventh Exemplary Embodiment

Figure 16:
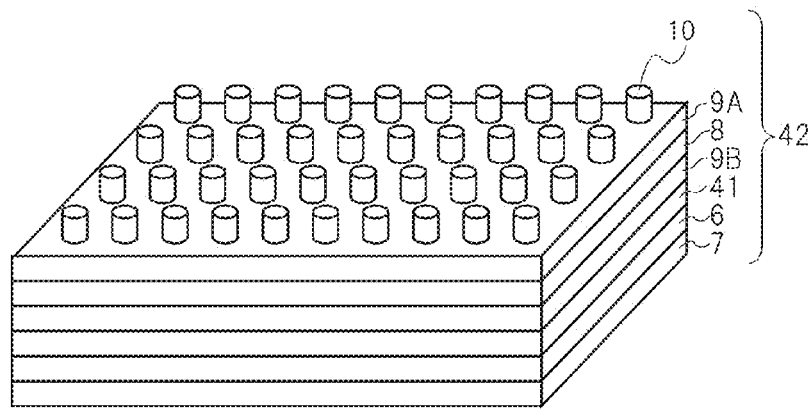
FIG. 16 is a schematic perspective view of the directivity control layer provided in the light source apparatus of the seventh exemplary embodiment.

FIG. 16 is a perspective view of a directivity control layer that is provided in the light source apparatus of the seventh exemplary embodiment. As shown in FIG. 16, directivity control layer 42 in the seventh exemplary embodiment is of the same configuration as directivity control layer 3 in the first exemplary embodiment, and differs in that another low dielectric constant layer 41 is provided between carrier-generating layer 6 and high dielectric constant layer 9B. In the present exemplary embodiment, the interface of low dielectric constant layer 7 and the light guide body (not shown) is the incident surface.

Eighth Exemplary Embodiment

Figure 17:
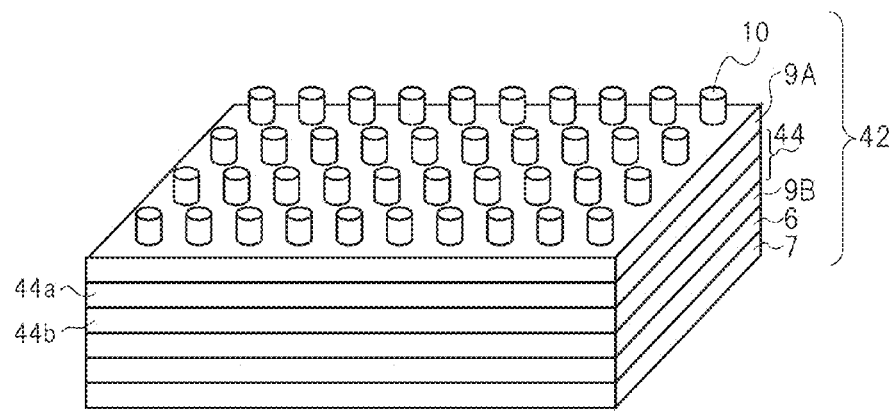
FIG. 17 is a schematic perspective view of the directivity control layer provided in the light source apparatus of the eighth exemplary embodiment.

FIG. 17 is a perspective view of the directivity control layer that is provided in the light source apparatus of the eighth exemplary embodiment. As shown in FIG. 17, directivity control layer 45 in the eighth exemplary embodiment is of the same configuration as directivity control layer 3 in the first exemplary embodiment but differs in that plasmon-excitation layer group 44 is made up of a plurality of stacked metal layers 44a and 44b. In the present exemplary embodiment, the interface of low dielectric constant layer 7 and the light guide body (not shown) is the incident surface.

In plasmon-excitation layer group 44 of directivity control layer 45 in the eighth exemplary embodiment, metal layers 44a and 44b are each formed by respectively differing metal materials and stacked, whereby plasmon-excitation layer group 44 is capable of adjusting the plasma frequency.

When implementing adjustment such that the plasma frequency in plasmon-excitation layer 44 increases, metal layers 44a and 44b are formed of, for example, Ag and Al, respectively. Alternatively, when implementing adjustment such that the plasma frequency in plasmon-excitation layer 44 decreases, differing metal layers 44a and 44b are formed of, for example, Ag and Au, respectively. Although a case is here shown in which plasmon-excitation layer group 44 is of a two-layer construction, plasmon-excitation layer 44 may of course be made up of three or more metal layers, as necessary.

In directivity control layer 45 of the eighth exemplary embodiment that is configured as described above, the construction of plasmon-excitation layer 44 by a plurality of metal layers 44a and 44b enables adjustment of the effective plasma frequency in plasmon-excitation layer 44 such that the effective plasma frequency approaches the frequency of light that is irradiated from carrier-generating layer 6 into plasmon-excitation layer 44. As a result, the utilization efficiency of light that is irradiated from light-emitting element 1 into optical element 51 can be further increased.

Ninth Exemplary Embodiment

Figure 18:
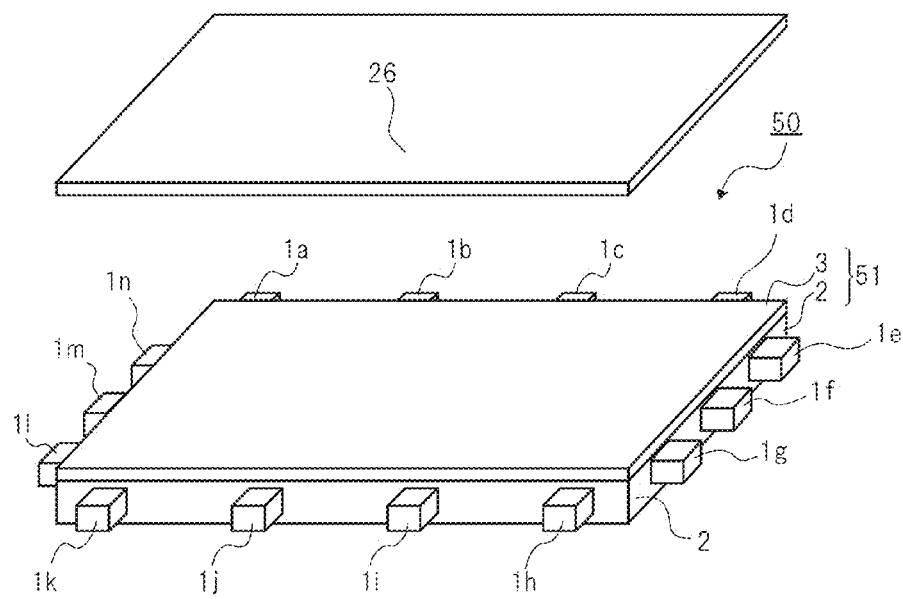
FIG. 18 is a perspective view showing the light source apparatus of the ninth exemplary embodiment.

FIG. 18 is a perspective view of the light source apparatus of the ninth exemplary embodiment. As shown in FIG. 18, in the light source apparatus of the ninth exemplary embodiment, as a polarization conversion element that converts axially symmetric polarized light that is irradiated from optical element 51 to a predetermined polarized state, axially symmetric polarization half-wave plate 26 is provided that linearly polarizes incident light from optical element 51. Converting light emitted from light source apparatus 50 to linearly polarized light by means of axially symmetric polarization half-wave plate 26 enables the realization of a light source apparatus in which the polarized state of the emitted light is uniform. When converting the axially symmetric polarized light to a uniform predetermined polarization state by means of a polarization conversion element, the present invention is not limited to linear polarization and also includes circular polarization. Still further, any of the directivity control layers in the above-described first to eighth exemplary embodiments may, of course, be applied as the directivity control layer.

Figure 19:
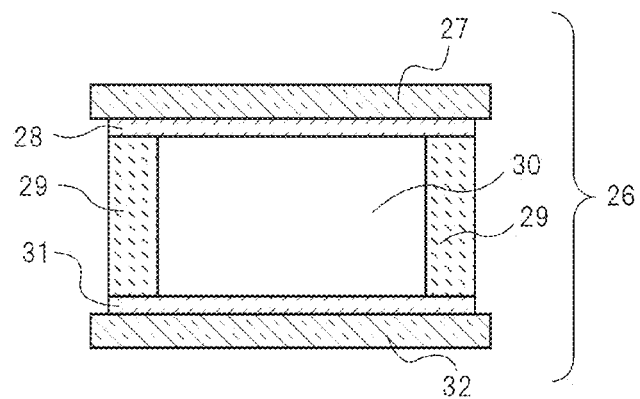
FIG. 19 is a vertical sectional view showing the construction of an axially symmetric polarization half-wave plate that is provided in the light source apparatus of the ninth exemplary embodiment.

FIG. 19 shows vertical sectional views of the construction of axially symmetric polarization half-wave plate 26. The configuration of the axially symmetric polarization half-wave plate is just an example and the present invention is not limited to this configuration. As shown in FIG. 19, axially symmetric polarization half-wave plate 26 is equipped with: a pair of glass substrates 27 and 32, orientation films 28 being formed on glass substrate 27 and orientation film 31 being formed on glass substrate 32; liquid crystal layer 30 that is arranged interposed between glass substrates 27 and 32 to face orientation films 28 and 31 of these glass substrates 27 and 32; and spacers 29 arranged between glass substrates 27 and 32.

Regarding liquid crystal layer 30, assuming that the index of refraction with respect to ordinary light is no, and the index of refraction with respect to extraordinary light is ne, the index of refraction ne is greater than the index of refraction no. Thickness d of liquid crystal layer 30 satisfies (ne−no)× d=λ/2. The value λ is the wavelength of incident light in a vacuum.

Figure 20:
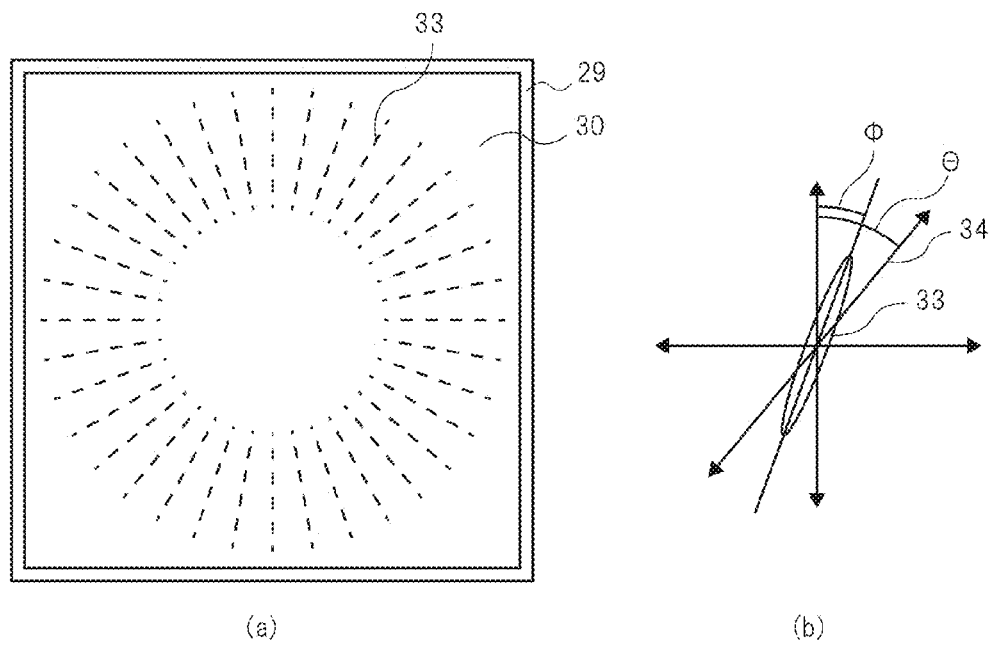
FIG. 20 (a)-(b) are schematic views for describing the axially symmetric polarization half-wave plate that is provided in the light source apparatus of the ninth exemplary embodiment.

FIGS. 20(a) and 20(b) are schematic views for describing axially symmetric polarization half-wave plate 26. FIG. 20(a) shows a horizontal sectional view of the state of cutting liquid crystal layer 30 of axially symmetric polarization half-wave plate 26 parallel to the principal surface of glass substrate 32. FIG. 20(b) is a schematic view for describing the direction of orientation of liquid crystal molecules 33.

As shown in FIG. 20(a), liquid crystal molecules 33 are oriented in concentric circles with respect to the center of axially symmetric polarization half-wave plate 26. As shown in FIG. 20(b), if the angle formed by the principal axis of liquid crystal molecule 33 and the coordinate axis that is close to this principal axis is φ, and if the angle formed by the direction of polarization and the coordinate axis is θ, then liquid crystal molecule 33 will be oriented in a direction that satisfies one of the relational expressions θ=2φ or θ=2φ−180. Here, FIG. 20(a) and FIG. 20(b) show the same surface.

Figure 21:
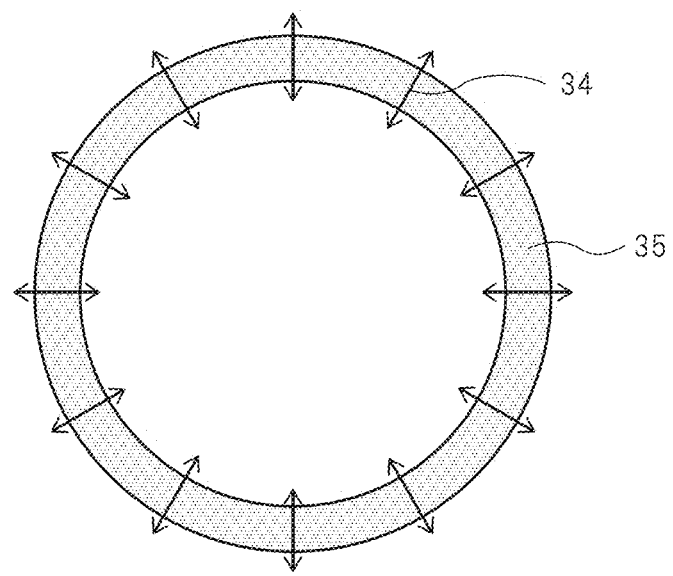
FIG. 21 is a schematic view showing the far-field pattern and polarization direction of light emitted for the case of a configuration not provided with an axially symmetric polarization half-wave plate in the light source apparatus of the exemplary embodiment.

FIG. 21 shows far-field pattern 35 of light emitted in the case of a configuration in which a light source apparatus is not provided with an axially symmetric polarization half-wave plate. In the above-described first to eighth exemplary embodiments, polarized light that produces plasmon coupling in plasmon-excitation layer 8 is only P-polarized light, and far-field pattern 35 of the light emitted from the light source apparatus is therefore axially symmetric polarized light in which the direction of polarization is radial as shown in FIG. 21.

Figure 22:
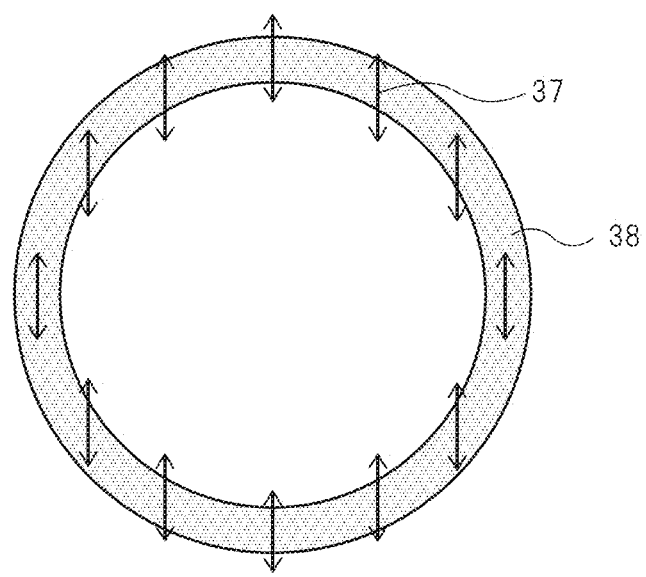
FIG. 22 is a schematic view showing the far-field pattern and polarization direction of light that is emitted in the case of a configuration provided with an axially symmetric polarization half-wave plate in the light source apparatus of the exemplary embodiment.

FIG. 22 shows far-field pattern 38 of the emitted light that has passed through axially symmetric polarization half-wave plate 26. Due to the use of above-described axially symmetric polarization half-wave plate 26 according to the present exemplary embodiment, emitted light is obtained in which polarization direction 37 is uniform as shown in FIG. 22.

First Working Example

Figure 23:
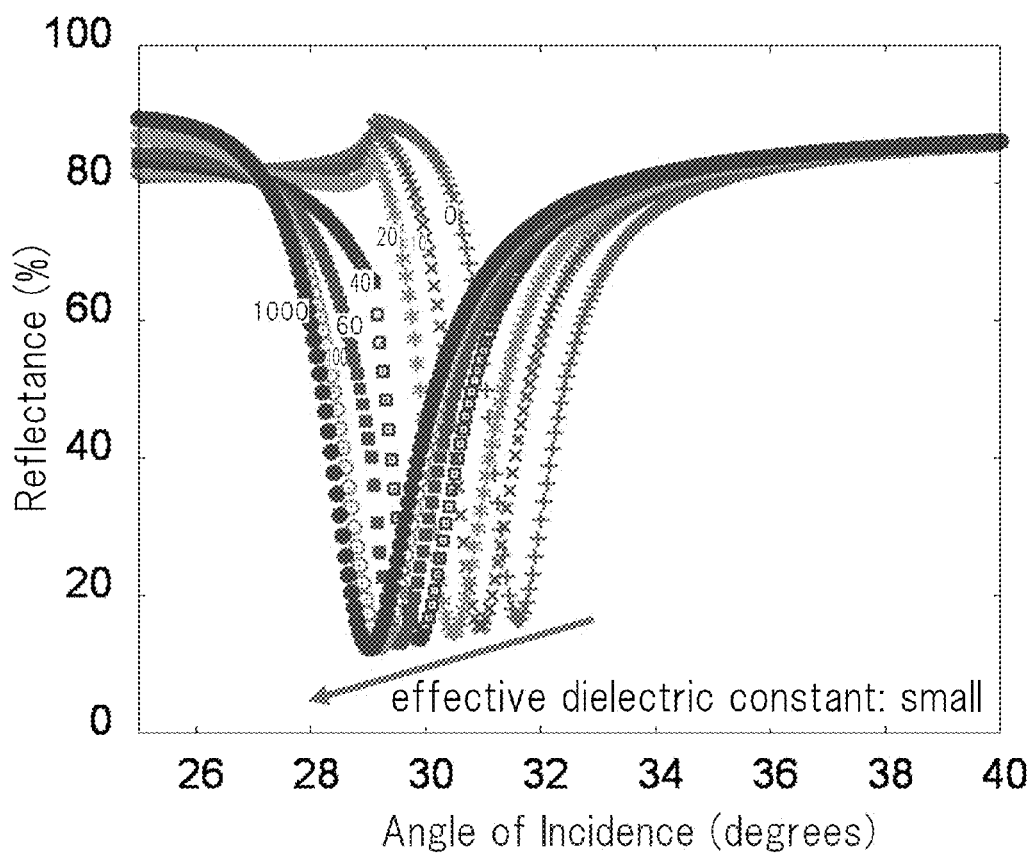
FIG. 23 is a view for describing the plasmon resonance property in the present invention.

FIG. 23 is a view for describing plasmon resonance characteristics in the above-described exemplary embodiments. FIG. 23 shows the relation of reflectance with respect to the angle of incidence for a case in which light of wavelength 460 nm is irradiated into each plasmon-excitation layer 8 in a light source apparatus in which $TiO_2$ is used for high dielectric constant layer 9A, porous $SiO_2$ is used for high dielectric constant layer 9B, Ag is used for plasmon-excitation layer 8, and air is used for low dielectric constant layer 7. Here, high dielectric constant layer 9A and low dielectric constant layer 7 were formed sufficiently thicker than the wavelength of light. FIG. 23 shows the angle of incidence and the reflectance for each case in which the thickness of high dielectric constant layer 9B was made 0 nm, 10 nm, 20 nm, 40 nm, 60 nm, 100 nm, and 1000 nm.

As shown in FIG. 23, the precipitous drop in reflectance when the angle of incidence is in the vicinity of 29-30 degrees can be understood to be due to coupling with plasmons because this angle is greater than the total reflectance angle. Thus, from the present working example, it can be seen it can be seen that, as high dielectric constant layer 9B increases, the effective dielectric constant decreases and the angle of incidence at which plasmons resonate decreases.

Figure 24:
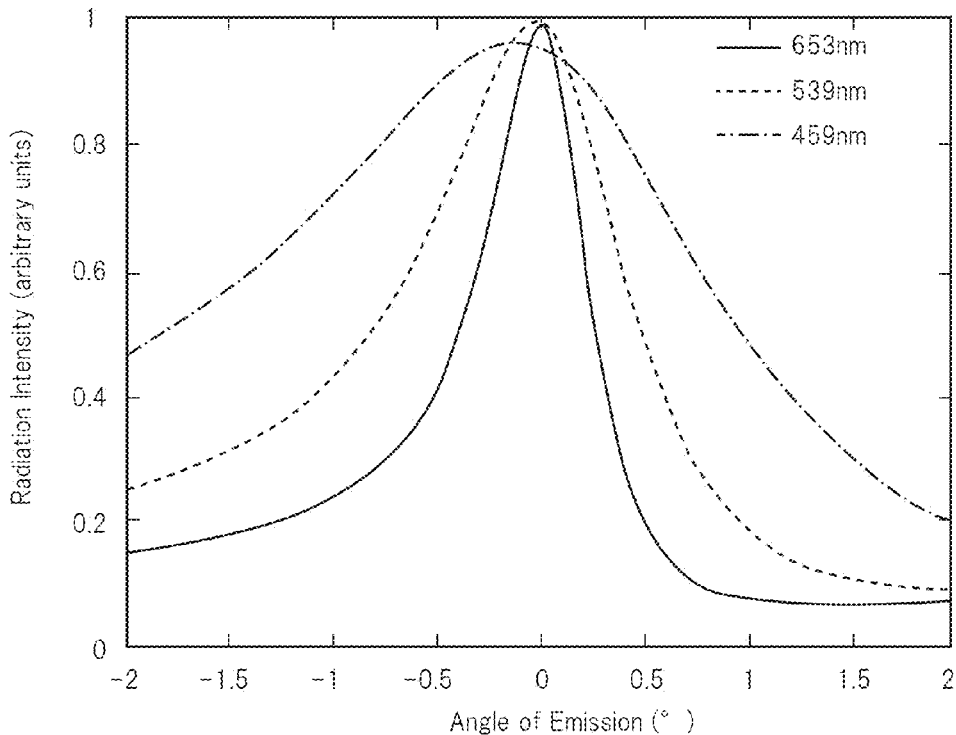
FIG. 24 is a view for describing the radiation angle property in the present invention.

FIG. 24 is a view for describing radiation angle characteristics in the above-described exemplary embodiments. FIG. 24 shows the angular distribution of light emitted from light-emission part 5 in a case in which light of each of wavelengths 653 nm, 539 nm, 459 nm from light-emitting element 1 is irradiated into a directivity control layer in a light source apparatus in which $TiO_2$ is used for high dielectric constant layer 9A, porous $SiO_2$ is used for high dielectric constant layer 9B, Ag is used for plasmon-excitation layer 8, and air is used for low dielectric constant layer 7.

In the interest of simplification, calculation was carried out in two dimensions. When the total width of the angle at which the intensity of light emitted from a light source apparatus becomes one-half is taken as the radiation angle, the radiation angle is 0.67 degrees, 1.3 degrees, and 3.0 degrees for light having a wavelength of 653 nm, 539 nm, and 459 nm, respectively. Here the grating pitch of the photonic crystal that makes up wave vector conversion layer 10 is set to 583 nm, 471 nm, and 386 nm for light having a wavelength of 653 nm, 539 nm, and 459 nm, respectively.

As shown above, the light source apparatus of the present exemplary embodiment is able to raise the directivity of the radiation angle of emitted light from the light source apparatus by utilizing plasmon-excitation layer 8, and moreover, is able to narrow the radiation angle to ±5 degrees or less to obtain a further increase in directivity by appropriately adjusting the grating structure of wave vector conversion layer 10.

Second Working Example

Figure 25:
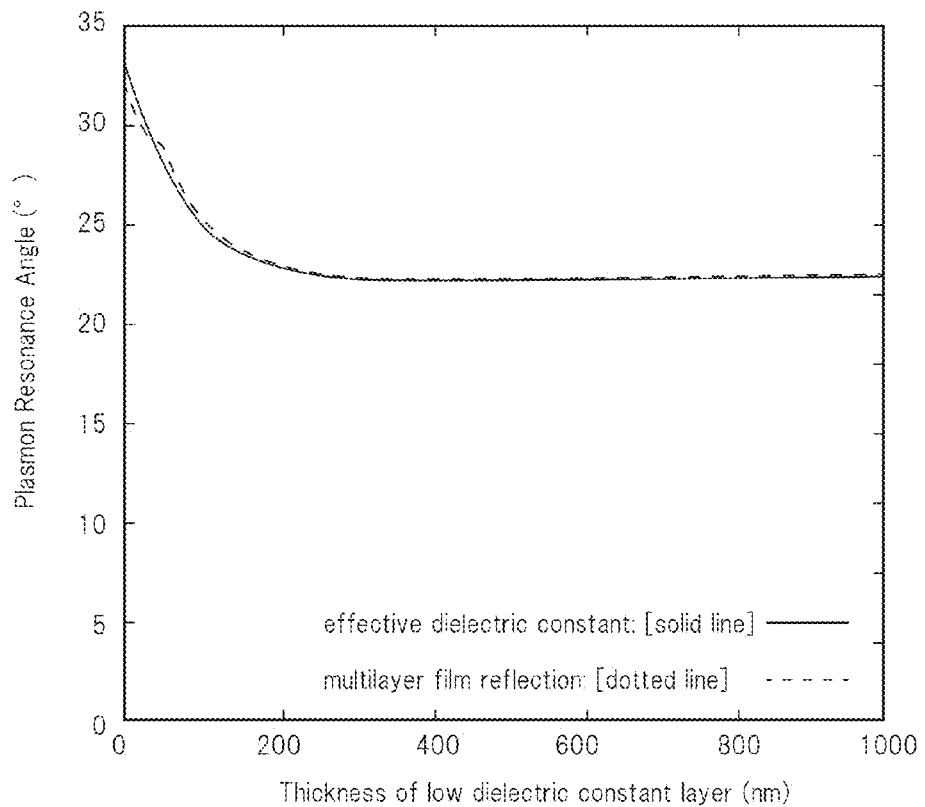
FIG. 25 shows a comparison of plasmon resonance angles determined by the effective dielectric constant and plasmon resonance angles determined by multilayer film reflection calculation in the light source apparatus of the first exemplary embodiment.

FIG. 25 shows a comparison of the plasmon resonance angle that is found from the effective dielectric constant that was calculated using Equation (1) and the plasmon resonance angle that is found by multilayer film reflection calculation in light source apparatus 50 of the first exemplary embodiment. In FIG. 25, the horizontal axis shows the thickness of high dielectric constant layer 9B, and the vertical axis shows the plasmon resonance angle. As clearly shown in FIG. 25, the value calculated by the effective dielectric constant matches the value calculated by multilayer film reflection, and the conditions of plasmon resonance can be defined by the effective dielectric constant that is defined by Equation (1).

$SiO_2$ was used as light guide body 2, a fluorescent material that uses PVA (Polyvinyl Alcohol) as a basic material was used as carrier-generating layer 6, air was used as low dielectric constant layer 7, Ag was used as plasmon-excitation layer 8, $TiO_2$ was used as high dielectric constant layer 9A, and porous $SiO_2$ was used as high dielectric constant layer 9B; the thicknesses of these layers being 0.5 mm, 70 nm, 0.1 mm, 50 nm, 0.5 mm, and 10 nm, respectively. In addition, calculation was carried out assuming an emission wavelength of carrier-generating layer 6 of 460 nm. Here, the material of wave vector conversion layer 18 was $TiO_2$; and the depth, pitch, and duty ratio of the periodic structure was set to 200 nm, 280 nm, and 0.5, respectively. Under these conditions, the light that is emitted has light distribution of a Gaussian function shape rather than being annular, but by shifting the pitch from 280 nm, the peak splits and an annular orientation distribution is obtained.

Figure 26:
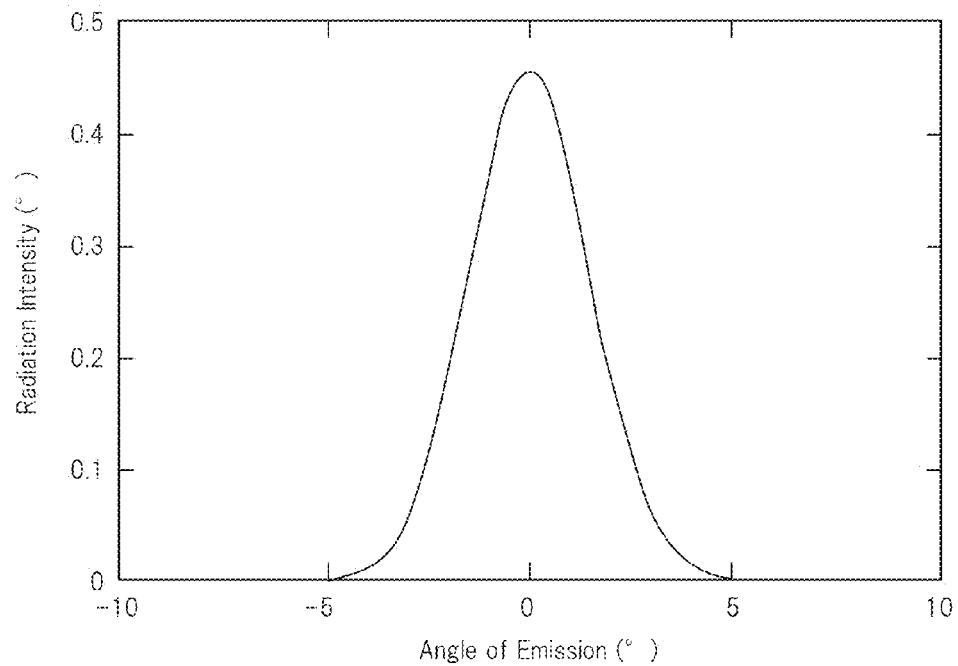
FIG. 26 shows the angle distribution in the light emitted of the light source apparatus of the first exemplary embodiment.

FIG. 26 shows the angular distribution in the light emitted from of light source apparatus 50 of the first exemplary embodiment that was calculated by taking into account the thicknesses of each of the above-described layers. In FIG. 26, the horizontal axis shows the angle of emission of light that is emitted and the vertical axis shows the intensity of emitted light.

In the interest of simplification, calculation was carried out in two dimensions. When the total width of the angle at which the intensity of light emitted from optical element 50 becomes one-half is taken as the radiation angle, the radiation angle is ±1.7 (degrees) for light having a wavelength of 460 nm.

Accordingly, light source apparatus 50 not only enables an improvement of the directivity of the radiation angle of light emitted from light source apparatus 50, but also enables narrowing of the radiation angle to +/− degrees or less to further raise directivity, through appropriate adjustment through appropriate adjustment of the grating structure of wave vector conversion layer 10.

In the second working example, the effective dielectric constants of the emission-side portion and incident-side portion of plasmon-excitation layer 8 are 9.8 and 2.0, respectively, according to Equation (1). The imaginary parts of the wave number of the z-direction on the emission side and incident side of surface plasmons are 0 and $1.28 \times 10^7$, respectively according to Equation (2). If the effective interactive distance of surface plasmons is assumed to be the distance at which the intensity of surface plasmons becomes $e^{-2}$, the effective interactive distances of surface plasmons of the emission-side portion and the incident-side portion are infinity and 78 nm, respectively, according to $1/\text{Im}(k_{spp,z})$.

Third Working Example

Figure 27:
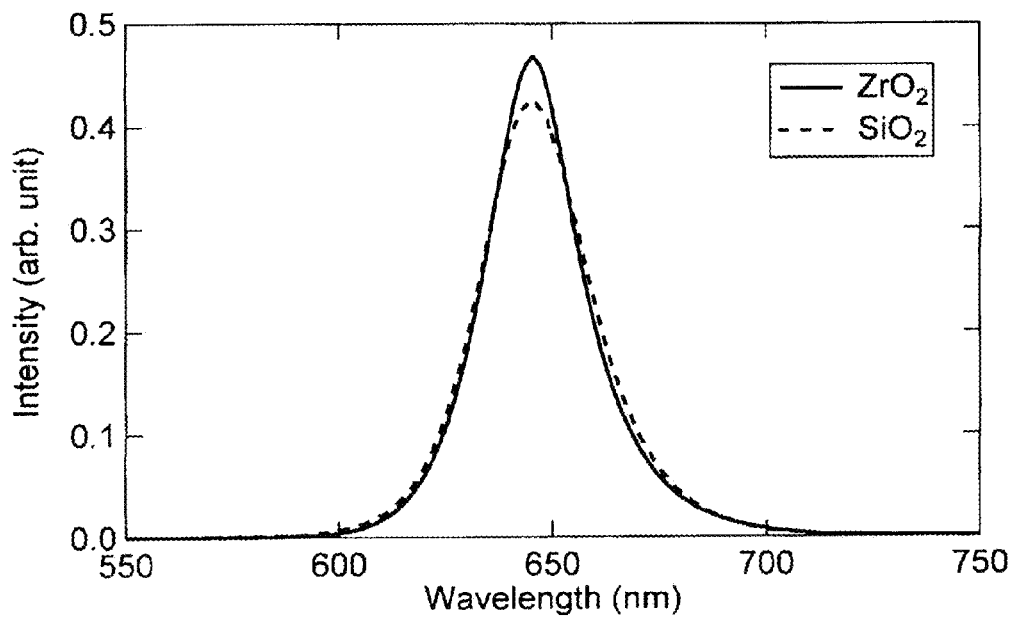
FIG. 27 shows the higher luminance effect realized by providing high-dielectric constant layer 9B.

FIG. 27 shows the effect of raising luminance through the provision of high dielectric constant layer 9B. The horizontal axis shows the wavelength of light, and the vertical axis shows the light intensity. In addition, the spectrums are compared for each angle at which the intensity of the light that is emitted reaches a peak. Air was used as light guide body 2 and as low dielectric constant layer 7, a quantum-dot fluorescent material in which the peak wavelength of emitted light was 640 nm was used as carrier-generating layer 6, $ZrO_2$ (dielectric constant: 4) or $SiO_2$ (dielectric constant 2.2) was used as high dielectric constant layer 9B, Ag was used as plasmon-excitation layer 8, and $TiO_2$ was used as high dielectric constant layer 9A; and the thicknesses of each layer were set to infinity, infinity, 40 nm, 10 nm, 50 nm, and 0.5 mm, respectively. A hemispherical lens having a diameter of 10 mm and refractive index of 2.0 was used as wave vector conversion layer 10, and a laser diode having a wavelength of 440 nm was used as the excitation light.

Higher light intensity, i.e., higher luminance, was obtained by using $ZrO_2$, which has a higher dielectric constant, as high dielectric constant layer 9B than by using $SiO_2$, which has a lower dielectric constant. In addition, as a secondary effect, the emission spectrum was narrowed. This narrowed spectrum is a desirable effect for uses where the color purity of emitted light is required.

The light source apparatus of the present exemplary embodiment is suitable for use as the light source apparatus of an image display device, and may be used as the light source apparatus that is provided in a projection-type display device, the directly-below light source apparatus of a liquid crystal panel (LCD), or as what is referred to as a backlight in electronic devices such as portable telephones or PDAs (Personal Data Assistants).

Figure 28:
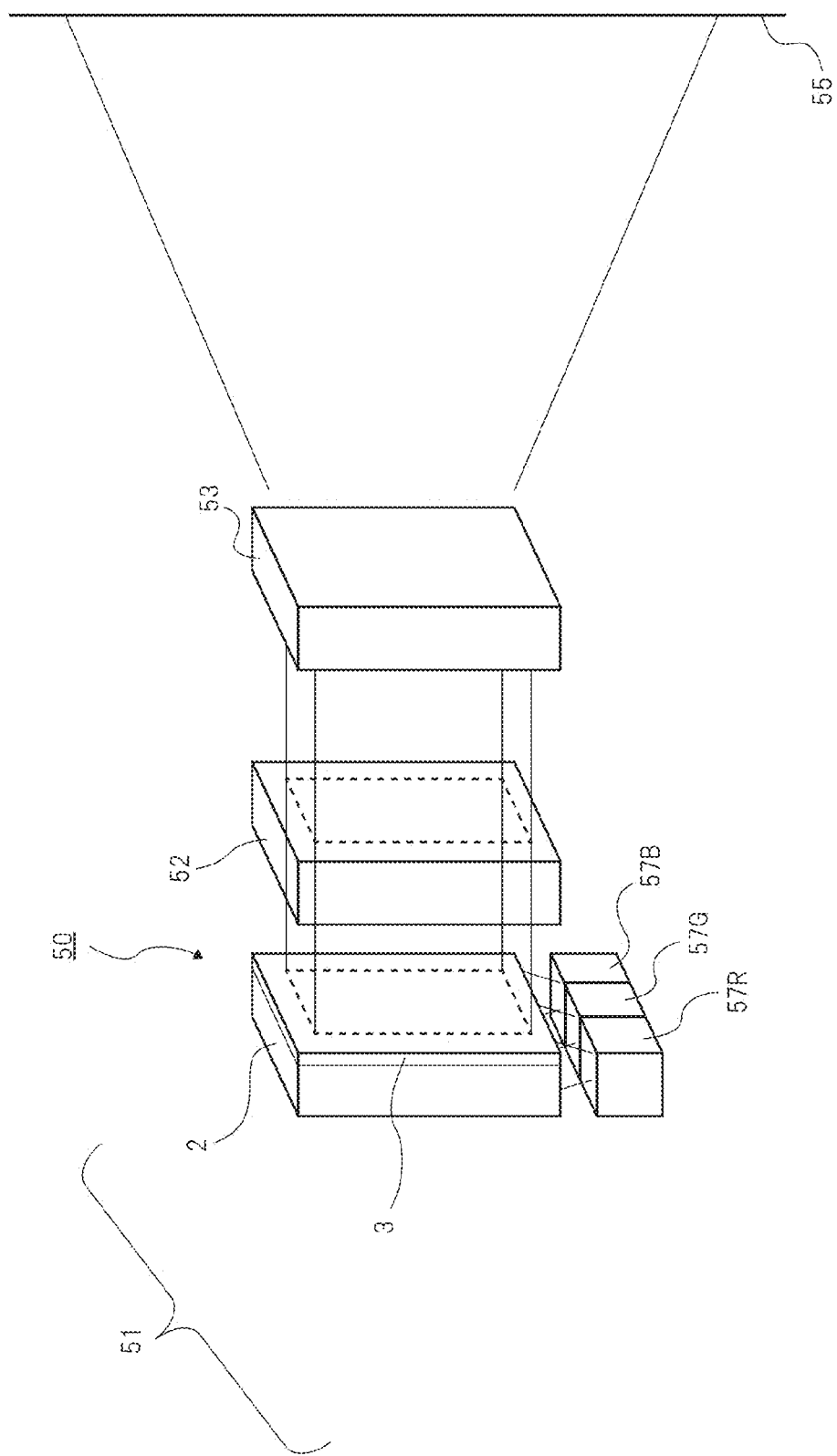
FIG. 28 is a schematic view showing an LED projector in which the light source apparatus of an exemplary embodiment is applied.

Finally, an LED projector is briefly described as a projection-type display apparatus in which the light source apparatus of the above-described exemplary embodiments is applied. FIG. 28 is a schematic view of a projection-type display apparatus of the exemplary embodiment.

As shown in FIG. 28, an LED projector of the exemplary embodiment is equipped with optical element 51 of the above-described exemplary embodiments, liquid crystal panel 52 into which light emitted from this optical element 51 is irradiated, and projection optical system 53 that includes projection lenses that project light emitted from this liquid crystal panel 52 onto projection surface 55 such as a screen.

In light source apparatus 50 that is provided in the LED projector, LED 57R for red (R) light, LED 57G for green (G) light, and LED 57B for blue (B) light are each arranged on a side surface of light guide body 2 that is provided with the directivity control layer. The carrier-generating layer included in the directivity control layer of light source apparatus 50 includes fluorescent material for red (R) light, green (G) light, and blue (B) light.

Figure 29:
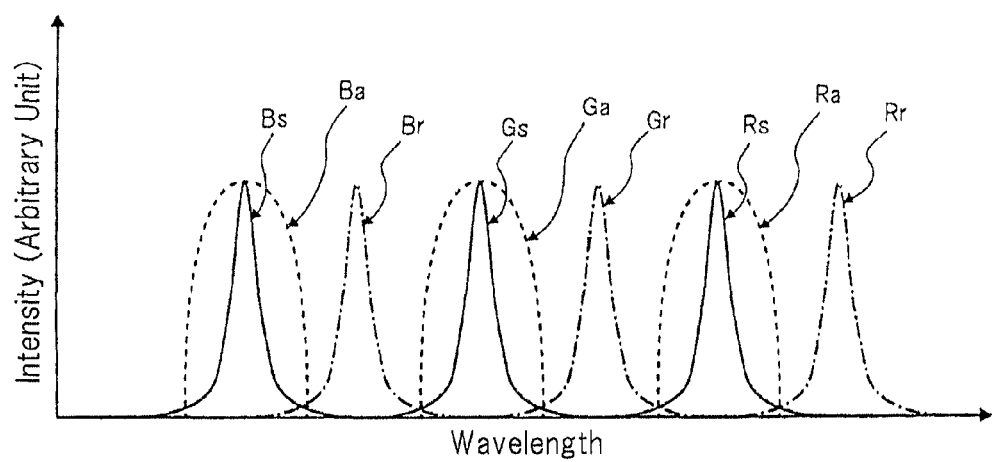
FIG. 29 is a view for describing the excitation wavelength and emitted light wavelength of fluorescent material and the wavelength of the light source used in the LED projector in which the light source apparatus of the exemplary embodiments is applied.

FIG. 29 shows the relation between the wavelength of light-emitting elements 1 that are used in the LED projector of the exemplary embodiments and the intensity of the excitation wavelength and emission wavelength of the fluorescent material. As shown in FIG. 29, the emission wavelengths Rs, Gs, and Bs of R light LED 57R, G light LED 57G, and B light LED 57B are each set to be substantially equal to the excitation wavelengths Ra, Ga, and Ba, respectively, of the fluorescent material. In addition, these emission wavelengths Rs, Gs, and Bs and excitation wavelengths Ra, Ga, and Ba are set so as not to overlap with the emission wavelengths Rr, Gr, and Br, respectively, of the fluorescent material. Still further, the emission spectrums of each of R light LED 57R, G light LED 57G, and B light LED 57B are set to match the respective excitation spectrums of the fluorescent material or to be accommodated within the respective excitation spectrums. Finally, the emission spectrums of the fluorescent material are set so as to prevent virtually all overlap with any of the excitation spectrums of the fluorescent material.

In the LED projector, a time division mode is adopted and switching implemented by a control circuit unit (not shown) such that only one from among R light LED 57R, G light LED 57G, and B light LED 57B produces light.

According to the LED projector of the present exemplary embodiment, the provision of light source apparatus 50 of the above-described exemplary embodiments enables improving the luminance of projected images.

Although an example of the configuration of a single-panel liquid crystal projector has been presented as the LED projector of the exemplary embodiment, the present invention may of course be applied in a three-panel liquid crystal projector that is equipped with liquid crystal panels for each of R, G, and B.

Although the present invention has been described with reference to exemplary embodiments, the present invention is not limited to the above-described exemplary embodiments. The configuration and details of the present invention are open to various modifications within the scope of the present invention that will be clear to one of ordinary skill in the art, and combining exemplary embodiments, that are combinable, from among each of the exemplary embodiments, enables combined and increased effects that are characteristic of each single exemplary embodiment.

This application claims the benefits of priority based on Japanese Patent Application No. 2011-135032, for which application was submitted on Jun. 17, 2011, and Japanese Patent Application No. 2012-001322, for which application was submitted on Jan. 6, 2012, and incorporates by citation all of the disclosures of these applications.

What is claimed is:

1. An optical element comprising:
   an incident surface into which light is irradiated;
   a carrier-generating layer that is laminated on said incident surface and in which carriers are generated by light;
   a plasmon-excitation layer that is laminated on said carrier-generating layer and that has higher plasma frequency than the frequency of light that is generated when said carrier-generating layer is excited by light that is irradiated from said incident surface; and
   an emission layer that is laminated on said plasmon-excitation layer and that converts light irradiated from said plasmon-excitation layer to a predetermined angle of emission and emits the light;

wherein:
said plasmon-excitation layer is interposed between two layers having dielectric properties;
taking said plasmon-excitation layer as a border, the effective dielectric constant of the emission-side portion that is said emission-layer side is higher than the effective dielectric constant of the incident-side portion that is said carrier-generating layer side; and
the dielectric constant between said plasmon-excitation layer and said carrier-generating layer is higher than the dielectric constant between said carrier-generating layer and said incident surface.

2. The optical element as set forth in claim 1, wherein said effective dielectric constant is determined based on:
the dielectric constant distribution of the dielectric of said incident-side portion or said emission-side portion; and
the surface plasmon distribution of said incident-side portion or said emission-side portion with respect to the direction perpendicular to the interface with said plasmon-excitation layer.

3. The optical element as set forth in claim 1, wherein:
where effective dielectric constant $\varepsilon_{eff}$ is said effective dielectric constant, the x-axis and the y-axis are directions parallel to the interface with said plasmon-excitation layer and the z-axis is a direction perpendicular to the interface with said plasmon-excitation layer, ω is the angular frequency of light that is emitted from said carrier-generating layer, $\varepsilon(\omega, x, y, z)$ is the dielectric constant distribution of the dielectric of said incident-side portion or said emission-side portion, integration range D is the three-dimensional coordinate range of said incident-side portion or said emission-side portion, $k_{spp,z}$ is the z-component of the wave number of surface plasmons, and j is an imaginary unit, then the effective dielectric constant $\varepsilon_{eff}$ satisfies:

$$\varepsilon_{eff} = \frac{\iint_D \int \mathrm{Re}[\varepsilon(\omega, x, y, z)]\exp(2jk_{spp,z}z)}{\iint_D \int \exp(2jk_{spp,z}z)} \quad \text{equation (1)}$$

or $$\varepsilon_{eff} = \left(\frac{\iint_D \int \mathrm{Re}\left[\sqrt{\varepsilon(\omega, x, y, z)}\right]\exp(2jk_{spp,z}z)}{\iint_D \int \exp(2jk_{spp,z}z)}\right)^2 \quad \text{equation (1.1)}$$

and moreover, where $\varepsilon_{metal}$ is the real part of the dielectric constant of said plasmon-excitation layer and $k_0$ is the wave number of light in a vacuum, the z-component $k_{spp,z}$ of the wave number of surface plasmons and the x- and y-components $K_{spp}$ of the wave number of surface plasmons satisfy:

$$k_{spp,z} = \sqrt{\varepsilon_{eff}k_0^2 - k_{spp}^2} \quad \text{equation (2)}$$

$$k_{spp} = k_0 \mathrm{Re}\left[\sqrt{\frac{\varepsilon_{eff}\varepsilon_{metal}}{\varepsilon_{eff} + \varepsilon_{metal}}}\right]. \quad \text{equation (3)}$$

4. The optical element as set forth in claim 1, further comprising a dielectric constant layer that is provided adjacent to at least one of said emission side of said plasmon-excitation layer and said carrier-generating layer-side of said plasmon-excitation layer.

5. The optical element as set forth in claim 1, wherein said plasmon-excitation layer is made up by stacking a plurality of metal layers composed of different metal materials.

6. The optical element as set forth in claim 1, wherein said plasmon-excitation layer is composed of any one of Ag, Au, Cu, Al and Pt or an alloy that contains at least one of these elements.

7. The optical element as set forth in claim 1, further comprising another plasmon-excitation layer that is provided between said incident surface and said carrier-generating layer and that has a plasma frequency that is higher than the frequency of said light-emitting element.

8. The optical element as set forth in claim 1, wherein said emission layer has a surface periodic structure.

9. The optical element as set forth in claim 1, wherein said emission layer is composed of photonic crystal.

10. The optical element as set forth in claim 1, wherein said low dielectric constant layer is air that is hermetically sealed by support columns.

11. A light source apparatus that uses the optical element as set forth in claim 1, comprising:
a light guide body that is laminated below said incident surface; and
a light-emitting element in which emitted light is irradiated to said light guide body.

12. The light source apparatus as set forth in claim 11, further comprising a polarization conversion element that converts axially symmetric polarized light that is incident from said optical element to a predetermined uniformly polarized state.

13. A projection-type display apparatus comprising:
the light source apparatus as set forth in claim 11; and
a projection optical system that projects projected images by means of the light emitted from said light source apparatus.

14. A light source apparatus that uses the optical element as set forth in claim 1, comprising:
an LED that takes as said incident surface the emission surface that emits light that is generated.

* * * * *